US010435660B2

(12) United States Patent
Seiler et al.

(10) Patent No.: US 10,435,660 B2
(45) Date of Patent: Oct. 8, 2019

(54) HANDLING DEVICE FOR A LABORATORY VESSEL

(71) Applicant: Hamilton Bonaduz AG, Bonaduz (CH)

(72) Inventors: Tobias Seiler, Flims Dorf (CH); Oliver Kühne, Malans (CH); Carsten Etzold, Bonaduz (CH)

(73) Assignee: Hamilton Bonaduz AG, Bonaduz (CH)

( * ) Notice: Subject to any disclaimer, the term of this patent is extended or adjusted under 35 U.S.C. 154(b) by 302 days.

(21) Appl. No.: 15/326,833

(22) PCT Filed: Jun. 3, 2015

(86) PCT No.: PCT/EP2015/062443
§ 371 (c)(1),
(2) Date: Jan. 17, 2017

(87) PCT Pub. No.: WO2016/008636
PCT Pub. Date: Jan. 21, 2016

(65) Prior Publication Data
US 2017/0198247 A1    Jul. 13, 2017

(30) Foreign Application Priority Data
Jul. 18, 2014  (DE) .................. 10 2014 214 076

(51) Int. Cl.
*C12M 1/00* (2006.01)
*F16M 11/18* (2006.01)
(Continued)

(52) U.S. Cl.
CPC ............ *C12M 29/00* (2013.01); *A61M 39/10* (2013.01); *B01L 3/567* (2013.01); *B01L 9/00* (2013.01);
(Continued)

(58) Field of Classification Search
CPC ...... C12M 29/00; C12M 23/08; C12M 23/38; C12M 23/40; C12M 23/50; A61M 39/10;
(Continued)

(56) References Cited

U.S. PATENT DOCUMENTS 5,163,902 A    11/1992  Lynn
2007/0133155 A1  6/2007  Zub
(Continued)

FOREIGN PATENT DOCUMENTS

DE    102013201069    7/2014
GB    2172093         9/1986
(Continued)

OTHER PUBLICATIONS

International Search Report dated Sep. 1, 2015.
German Search Report dated Feb. 27, 2015.

*Primary Examiner* — Benjamin R Whatley
(74) *Attorney, Agent, or Firm* — Rankin, Hill & Clark LLP

(57) ABSTRACT

A fluid line element for building a fluid line section comprising a plurality of identical fluid line elements, wherein the fluid line element comprises: —an element body, —a first throughflow opening provided on the element body and a second throughflow opening, different from the first, —and a flow channel provided in the element body, which fluidically connects the first and the second throughflow openings for throughflow along a channel path. In a first region of the fluid line element, located closer to the first than to the second throughflow opening, a throughflow body formed separately from the element body is provided, which —forms a part of the flow channel, —is formed from a material having a lower elasticity modulus than the material of the element body, and —on the longitudinal end thereof (Continued)

facing into the interior of the element body, comprises a valve seat formation surrounding the channel path.

11 Claims, 11 Drawing Sheets

(51) Int. Cl.
| | |
|---|---|
| *C12M 1/24* | (2006.01) |
| *B01L 3/00* | (2006.01) |
| *B01L 9/00* | (2006.01) |
| *F16M 11/10* | (2006.01) |
| *F16M 11/22* | (2006.01) |
| *A61M 39/10* | (2006.01) |

(52) U.S. Cl.
CPC ............... *B01L 9/50* (2013.01); *C12M 23/08* (2013.01); *C12M 23/38* (2013.01); *C12M 23/40* (2013.01); *C12M 23/50* (2013.01); *F16M 11/10* (2013.01); *F16M 11/18* (2013.01); *F16M 11/22* (2013.01); *B01L 2200/025* (2013.01); *B01L 2200/026* (2013.01); *B01L 2300/0864* (2013.01); *B01L 2400/06* (2013.01)

(58) Field of Classification Search
CPC .... B01L 3/567; B01L 9/00; B01L 9/50; B01L 2200/025; B01L 2200/026; B01L 2300/0864; B01L 2400/06; F16M 11/10; F16M 11/18; F16M 11/22

See application file for complete search history.

(56) References Cited

U.S. PATENT DOCUMENTS

| | | |
|---|---|---|
| 2007/0187634 A1 | 8/2007 | Sneh |
| 2007/0218757 A1 | 9/2007 | Guala |
| 2009/0137026 A1* | 5/2009 | Kobayashi ............. C12M 23/12 435/286.4 |
| 2011/0095217 A1* | 4/2011 | Schlenker ............. F16K 15/183 251/129.15 |
| 2011/0223076 A1 | 9/2011 | Wynn |
| 2013/0243651 A1* | 9/2013 | Oprea ..................... B01L 3/508 422/63 |
| 2014/0361041 A1 | 12/2014 | Hawken |
| 2015/0224237 A1* | 8/2015 | Reasoner ............ A61M 1/0023 604/320 |
| 2016/0186124 A1* | 6/2016 | Jager ..................... C12M 23/40 435/289.1 |
| 2016/0252537 A1* | 9/2016 | Murali .................. C12M 45/02 435/325 |

FOREIGN PATENT DOCUMENTS

| | | | |
|---|---|---|---|
| WO | 2011/090781 | 7/2011 | |
| WO | WO-2014114610 A1 * | 7/2014 | ............ C12M 23/40 |

\* cited by examiner

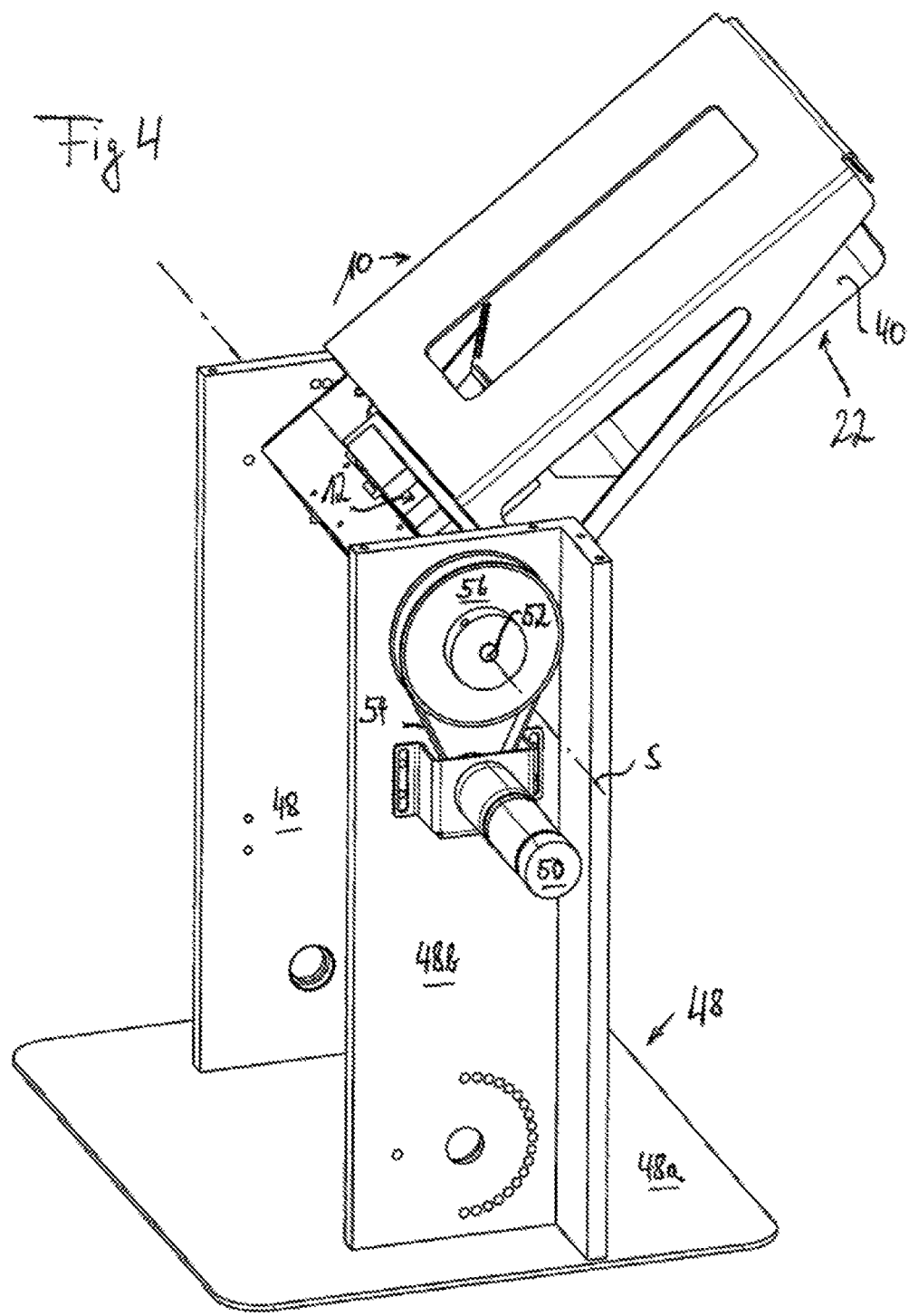

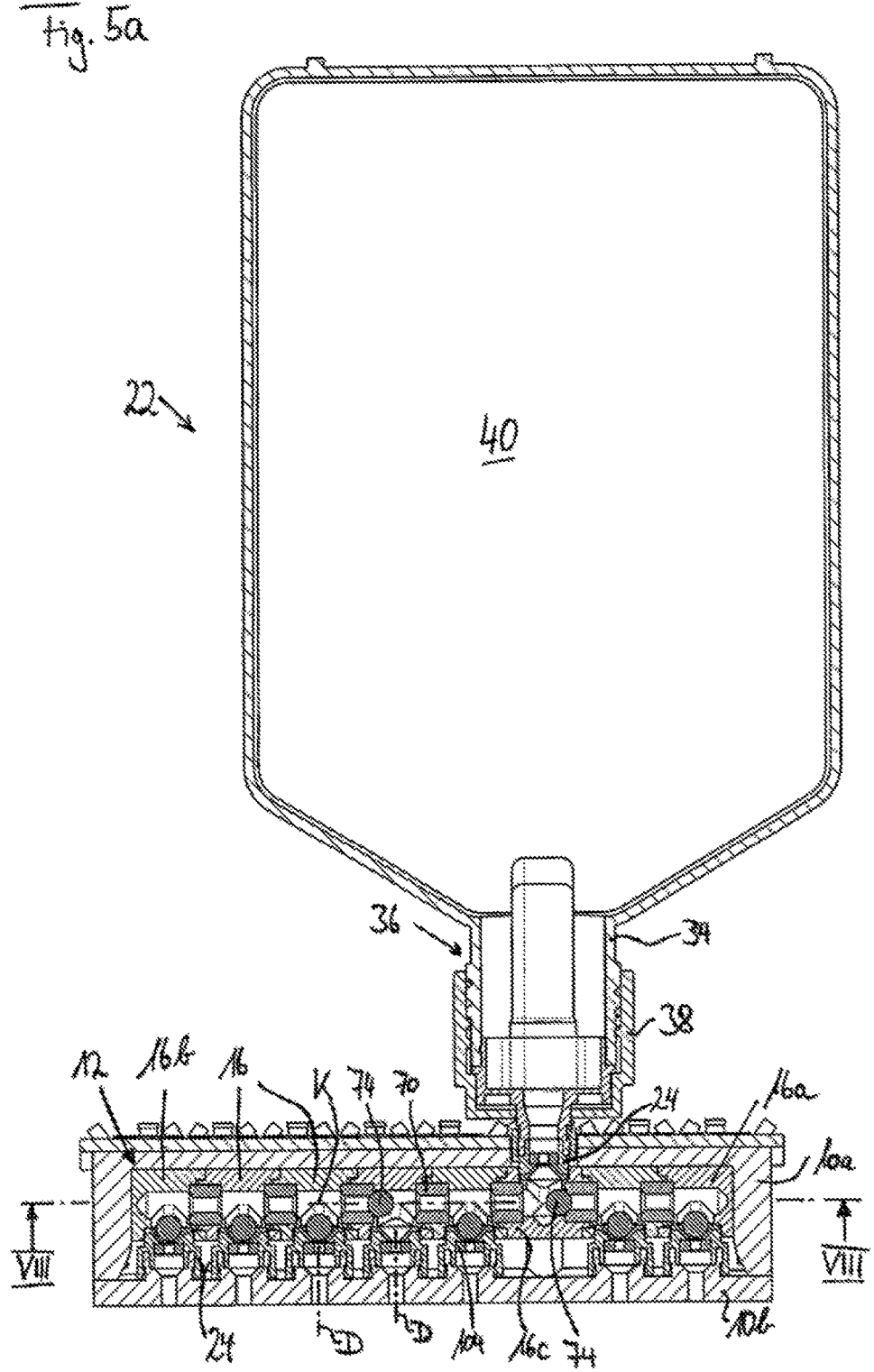

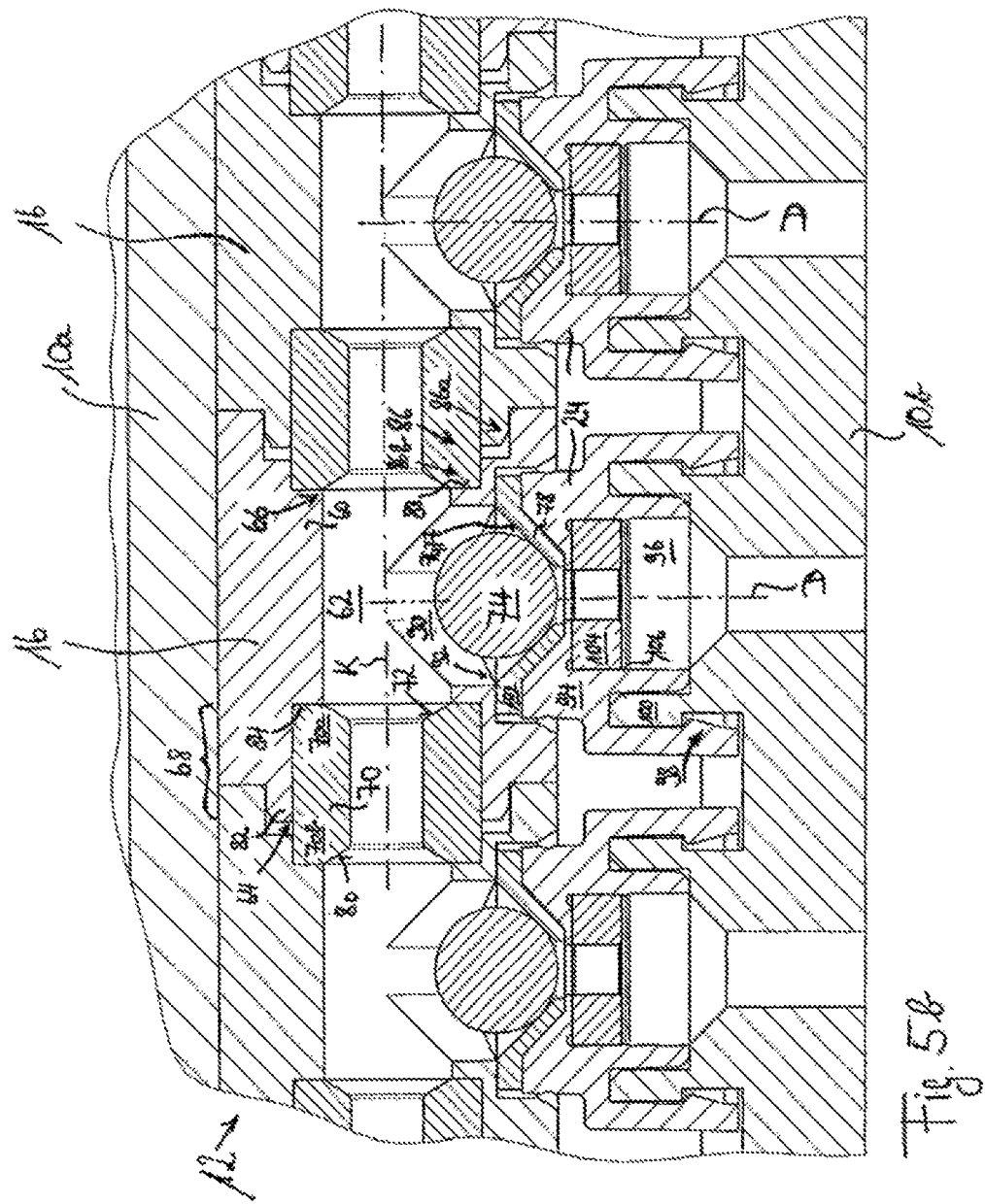

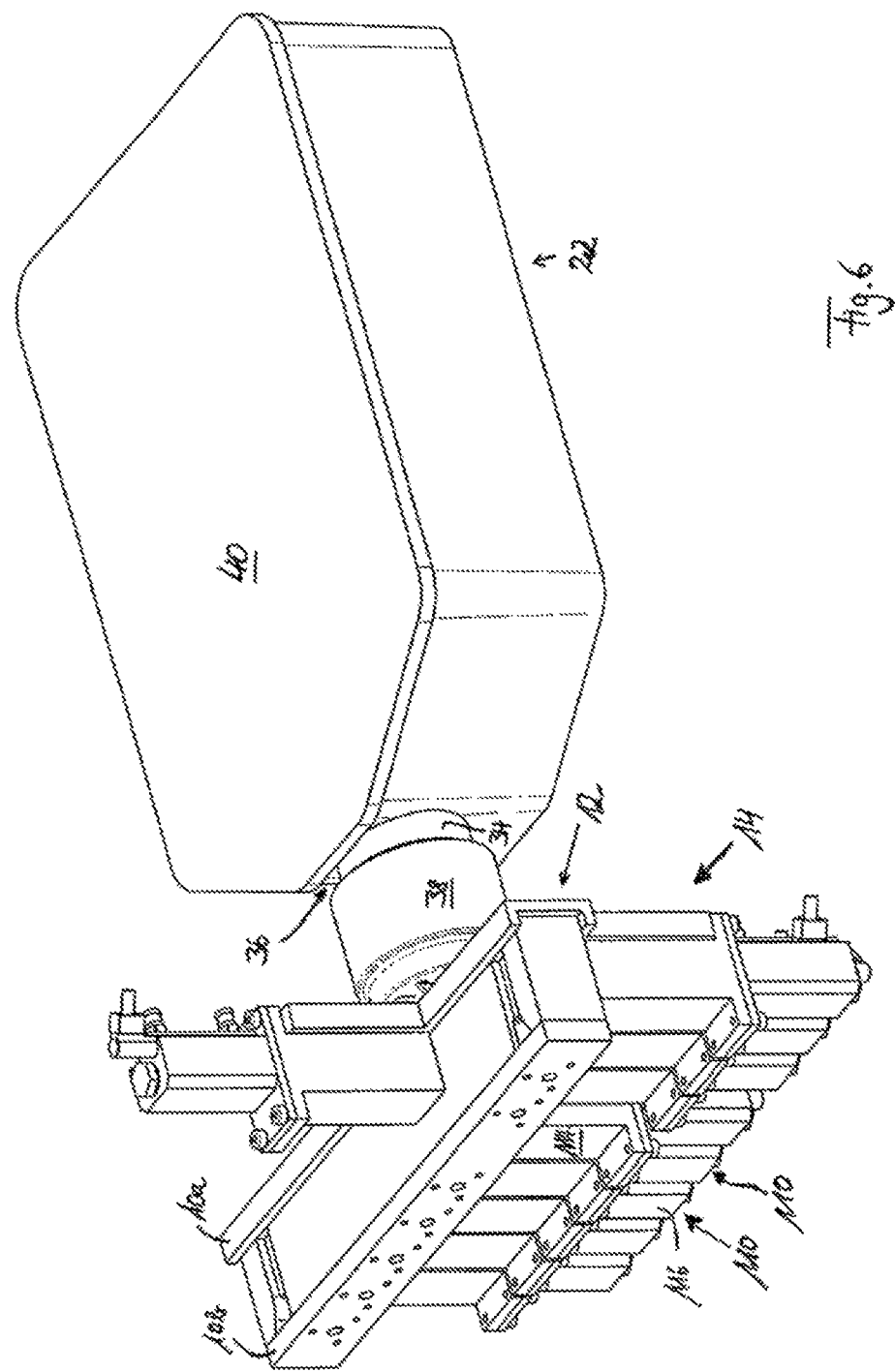

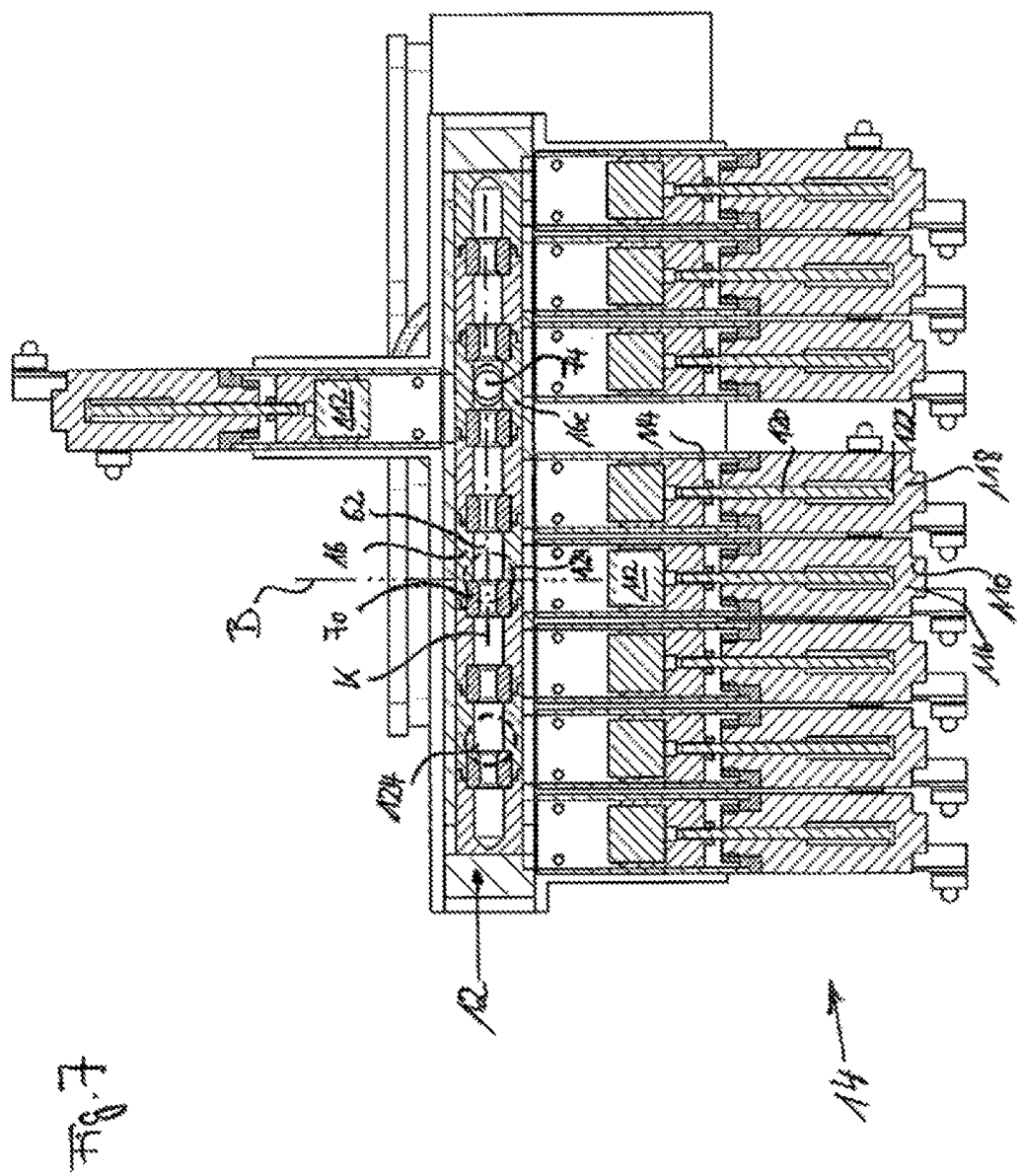

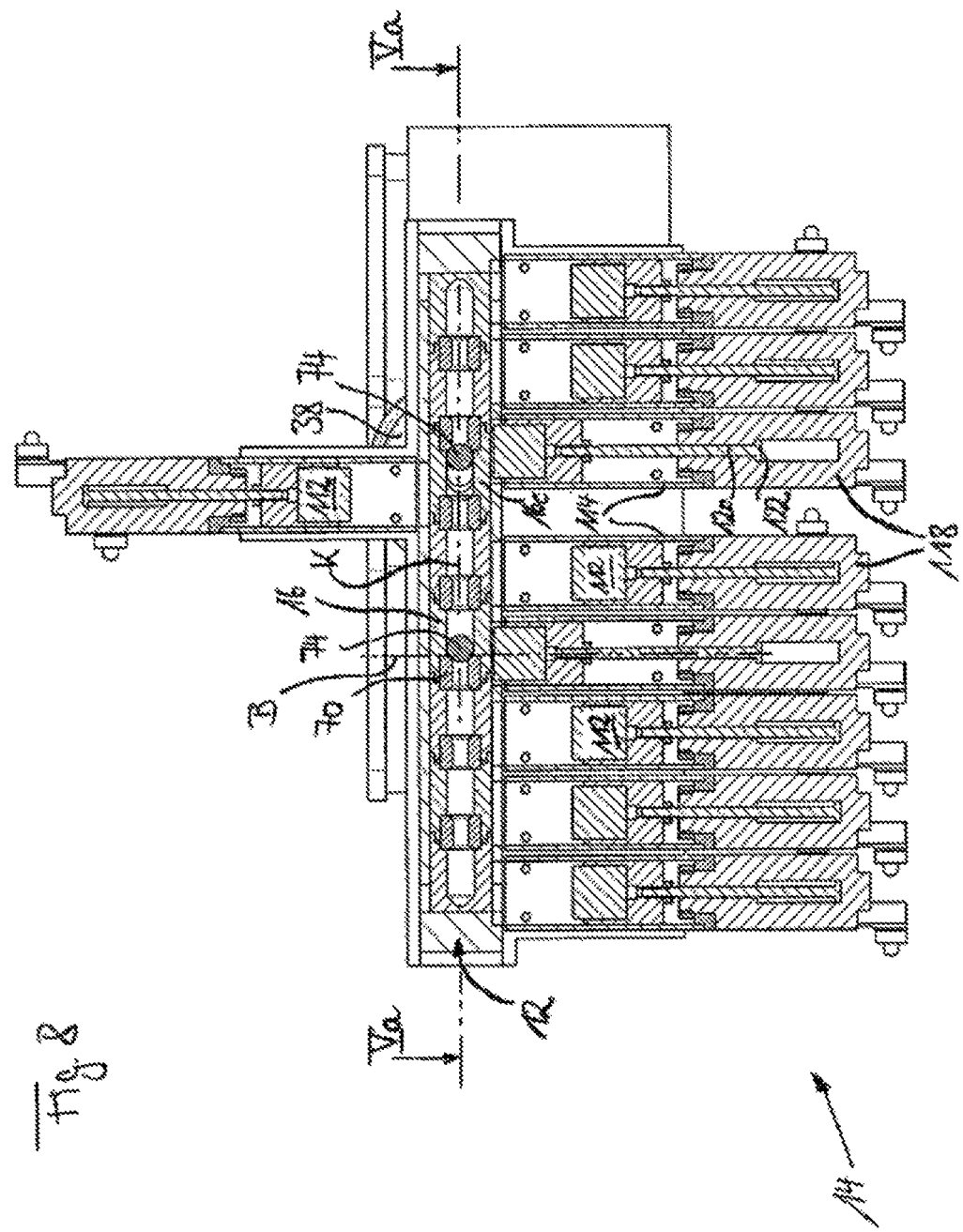

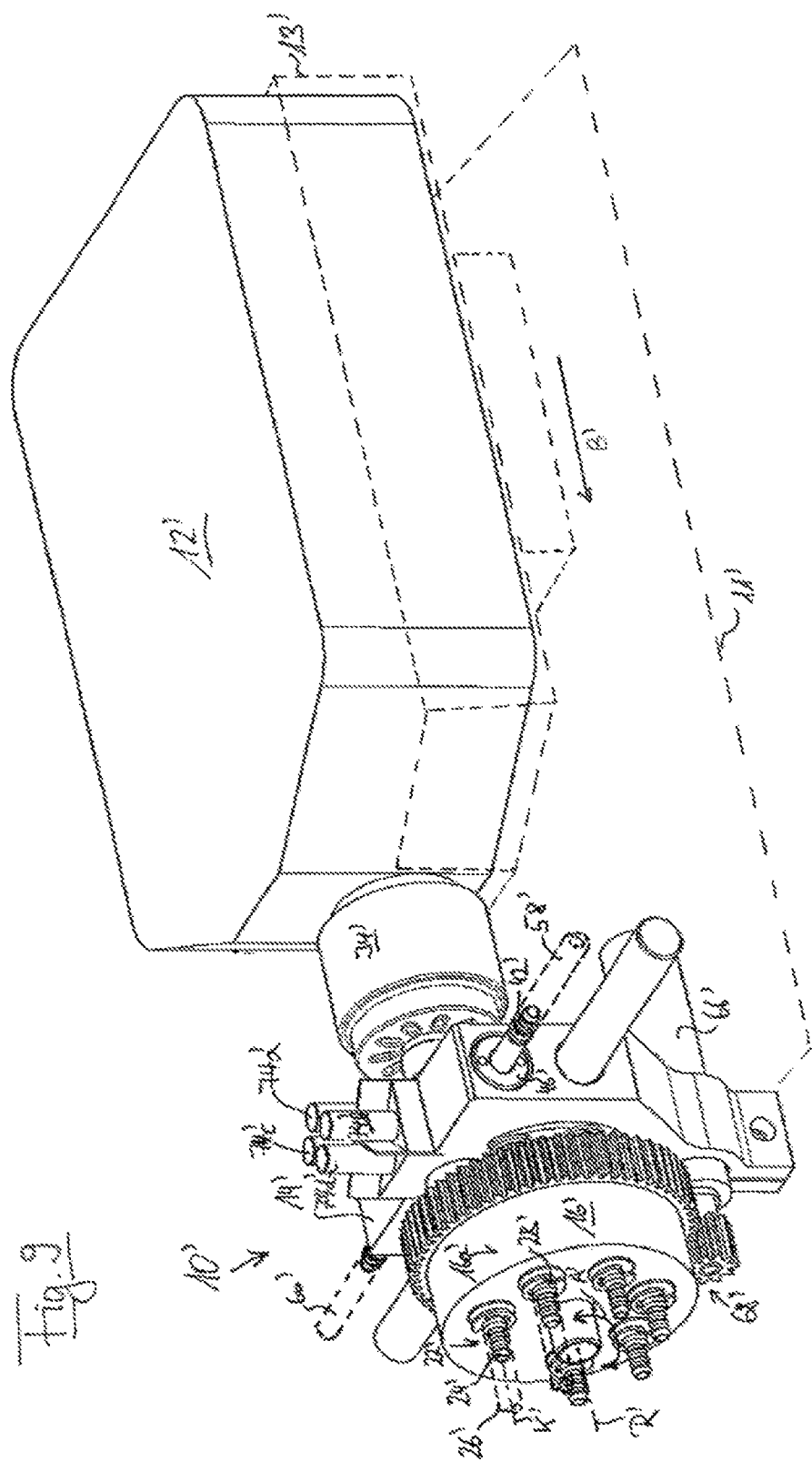

HANDLING DEVICE FOR A LABORATORY VESSEL

DESCRIPTION

The present invention relates to a fluid line element for building a fluid line section comprising a plurality of identical fluid line elements, wherein the fluid line element comprises an element body, a first throughflow opening provided on the element body, a second throughflow opening, different from the first one, provided on the element body, and a flow channel provided in the element body which fluidically connects the first and the second throughflow openings for throughflow along a channel path.

The present application moreover relates to a fluid line arrangement with at least one such fluid line element, preferably with a plurality of such fluid line elements.

Furthermore, the present invention relates to a valve line arrangement with a fluid line arrangement and a switching arrangement for switching at least one valve in the fluid line arrangement.

Finally, the present application relates to a handling device with a valve line arrangement.

A fluid line element according to the preamble is known, for example, from WO 2011/090781 A1 of the Millipore Corporation (US).

Figure 1:
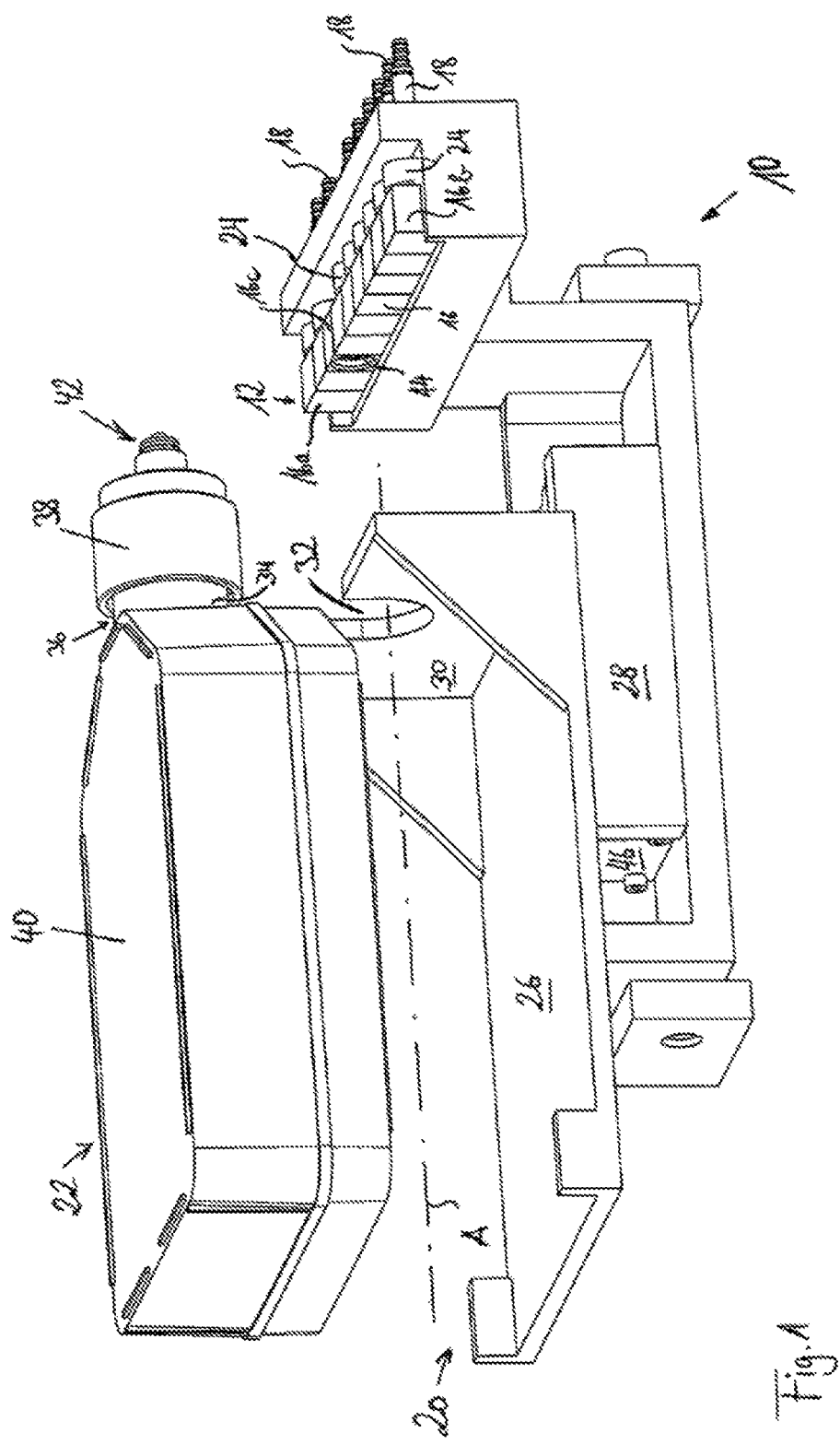

This published document discloses, for example, in its FIG. 1, a fluid line element according to the preamble, which is provided on the end side in the regions of the first and the second throughflow openings thereof in each case with a sterile connector.

A disadvantage of the known fluid line element is the requirement that it must be sterile. Another disadvantage is the complicated structure of a fluid line arrangement formed from the known fluid line elements, wherein fluid line elements directly adjacent along a channel path are in contact with the respective sterile connectors of the fluid line elements which face one another.

The aim of the present invention is to improve the fluid line element of the type known from the prior art, mentioned at the beginning, in the sense of attenuating or completely avoiding the above-mentioned disadvantages, and thus also to improve as a result fluid line arrangements formed from such fluid line elements.

The present aim is attained by a fluid line element according to the invention in which, in a first region of the fluid line element located closer to the first than to the second throughflow opening, a throughflow body formed separately from the element body is provided, which forms a part of the flow channel and is formed from a material having a lower elasticity modulus than the material of the element body, and which comprises, on the longitudinal end thereof facing the interior of the element body, a valve seat formation surrounding the channel path.

The throughflow body formed separately from the element body can be used for the sealing of the connection site with an additional identical fluid line element. For this purpose, it forms a part of the flow channel, and thus a medium flowing in the flow channel can flow through it. As a result, the possibility also exists of sterilizing the throughflow body as well as the throughflow channel of the fluid element at any time, for example, by running a suitable cleaning and/or sterilization medium through the flow channel and thus through the throughflow body forming a part thereof.

Since the throughflow body is formed moreover from a material which has a lower elasticity modulus than the material of the element body, the throughflow body, in the case of an otherwise identical external load, is more deformable than the element body, which makes the throughflow body suitable for use as a sealing element for the transition between two fluid line elements directly adjacent along the channel path.

Moreover, one throughflow body per fluid line element is sufficient in order to form a fluid line section extending along connected individual channel paths of several fluid line elements, since each fluid line element comprises a throughflow body which is located closer to the first than to the second throughflow opening and which is sufficient for sealing the connection to another fluid line element adjoining the first throughflow opening. Thus, for example, a fluid line section can be formed in that the first throughflow opening of a fluid line element is connected to the second throughflow opening of another fluid line element. The first-mentioned fluid line element here supplies the throughflow body which can be used for sealing the connection between the fluid line element and the additional fluid line element. The additional fluid line element in turn has a throughflow body on the first throughflow opening thereof, which in turn can be connected to the second throughflow opening of yet another fluid line element.

In order to ensure that a fluid line section formed from a plurality of fluid line elements is functional, the only thing that remains to be done is to suitably close the second throughflow opening on an end-side fluid line element, for example, by means of a stopper or by means of a fluid line element with a blind hole as flow channel.

Due to the formation of the flow body from a material having a lower elasticity modulus than the material of the element body, it is moreover possible to design the longitudinal end of the throughflow body pointing into the interior of the element body as a valve seat formation. This valve seat formation surrounds the channel path, so that the flow channel provided in the element body can be barred to throughflow by a valve body when the valve body is placed on the valve seat formation surrounding the channel path. However, the valve body does not have to be surrounded by the fluid line element.

Due to the above-described material selection, a valve body, in the movement thereof along the channel path, can be guided by the material of the element body having a higher elasticity modulus, while the valve seat formation on the throughflow body, due to the material with lower elasticity modulus selected for it, can be deformable by the valve body, in order to achieve the best possible sealing between valve seat formation and valve body.

For building a fluid line section from the above-mentioned fluid line elements, it can be sufficient, as already described above, to provide a throughflow body only in the first region, which is thus closer to the first throughflow opening than to the second throughflow opening. Therefore, a fluid line element that is preferable due to the particularly simple structure thereof can be designed in such a manner that the second throughflow opening, and a second region of the fluid line element, directly adjoining said second throughflow opening in the flow channel and extending along the channel path, second region which is located closer to the second than to the first throughflow opening, are free of throughflow bodies formed separately from the element body.

However, alternatively thereto, it can be helpful to design a fluid line element as a branching element, starting from which a fluid line section can extend away in different or even entirely opposite directions. The fluid line section can be formed by one fluid line element or a plurality of the above-mentioned fluid line elements. The branching element can be formed in that the two throughflow openings have a substantially identical structure, so that, both on the first throughflow opening and also on the second throughflow opening, a fluid line element as described above can be applied. For this purpose, it is conceivable that, also in a second region of the fluid element located closer to the second than to the first throughflow opening, a second throughflow body formed separately from the element body is provided, which forms a part of the flow channel, is made from a material having a lower elasticity modulus than the material of the element body, and comprises, on the longitudinal end thereof facing the interior of the element body, a valve seat formation surrounding the channel path.

The second throughflow body is preferably formed from the same material as the first throughflow body. In order to achieve the simplest possible manufacturing, the first and the second throughflow bodies are preferably built identically.

In order to ensure that the throughflow body can perform sealing functions both at the connection site of two fluid line elements for connecting the respective flow channels thereof to form a common fluid line section, and also in collaboration with a valve body, the throughflow body and/or the second throughflow body can comprise, according to a preferred development of the present invention, an elastomer material, in particular a rubber and/or silicone material. This can be implemented, for example, by coating a core made of a stiffer material. In order to achieve the simplest possible manufacturing, the throughflow body and/or the second throughflow body is/are preferably made from such a material. The material of the throughflow body and/or the second throughflow body is preferably not filled, in order to be able to achieve the highest possible degree of deformation with a predetermined load.

The sealing of a connection site between two fluid line elements directly adjacent along the channel path, for the purpose of the connection of the respective flow channels thereof to one another, can be improved in that the throughflow body and/or the second throughflow body protrude(s) along the channel path beyond the element body. Due to the protrusion of the throughflow body beyond the element body of the fluid line element supporting it, said throughflow body can be deformed by the element body of the additional fluid line element directly adjoining along the channel path and thus it can be arranged with increased sealing effect in the region between the two adjacent fluid line elements. The mentioned deformation can lead, for example, to the contact of the deformed throughflow body against sections surrounding it of one and/or of the other element body of the two fluid line elements adjacent along the channel path, preferably to a contact that completely surrounds the channel path. In the case of an appropriate contact force due to the resilient deformation of the throughflow body, this contact can prevent fluid flow between throughflow body and element body past the throughflow body.

The throughflow body protruding beyond the element body can abut, with the longitudinal end thereof located in the element body, against a ledge or a radial protrusion relative to the channel path—in such a manner that a shifting of the throughflow body along the channel path into the element body is prevented by this contact engagement. As a result, on the one hand, the position of the throughflow body along the channel path relative to the element body can be defined unequivocally. On the other hand, the element body with the radial protrusion or the ledge, can comprise an optional additional contact surface for the contact of the throughflow body on the element body of the fluid line element supporting it, on which the throughflow body achieves a sealing effect or flow barring effect due to resilient deformation.

Preferred developments of the present invention relating to the throughflow body also relate, without special separate mention, to the second throughflow body.

To achieve the most flexible possible use of the fluid line element, particularly with regard to the selection and implementation of a desired flow course through a fluid line arrangement which is formed by a plurality of fluid line elements, it is possible to provide that the throughflow body and/or the second throughflow body also comprise(s), on the longitudinal end thereof facing the outside environment of the fluid line element, an additional valve seat formation surrounding the channel path. Thus, in each case, the flow body can be used at the two longitudinal ends thereof as a valve seat. This does not mean that the throughflow body must in fact be used at each longitudinal end as a valve seat. However, at each longitudinal end thereof, the possibility then exists of moving a suitably shaped valve body in sealing contact and of removing it again from the respective valve seat formation.

The valve seat formation and/or the additional valve seat formation on the longitudinal end(s) of the throughflow body can be formed as a depression into which a valve body can be shifted. As a result, the possibility exists of creating a contact surface with sufficient extent along the channel path between valve body and valve seat formation, so that a sealing contact of the valve body on the respective valve seat formation with good flow barring effect can be achieved.

Preferably, the depression can be in the form of a tapering wall shape tapering from the respective longitudinal end of the throughflow body, which comprises the valve seat formation, along the channel path in the direction toward the respective other longitudinal end of the throughflow body. As a result, independently of the fabrication and shape tolerances of the valve body and/or of the wall shape, a sufficient contact surface of the valve body, which extends around the channel path continuously, on the valve seat formation can be ensured. The tapering wall shape is preferably a wall shape which tapers continuously along the channel path, that is to say a wall shape without discontinuities that could potentially have the effect of reducing the barring. The depression can thus be designed in the shape of a cone, in which case the channel path is then preferably the cone axis of the conical depression. However, the depression can also be formed as a negative spherical cap-shaped wall shape, which is particularly suitable for the use of spherical valve bodies that collaborate with the valve seat formation. However, the previously mentioned conical depression also achieves excellent flow barring effects in collaboration with spherical valve bodies.

For the defined connection of the flow channels of two fluid line elements, it can be advantageous if the fluid line element according to the invention comprises a collar which protrudes from the rest of the element body in the direction of the channel path and surrounds the channel path. The collar can surround the channel path in the form of a polygonal collar, or it can surround the channel path in the form of a continuously curved ring collar.

The collar can be provided on the first or on the second throughflow opening. However, the collar is preferably provided so that it surrounds the throughflow body and/or the second throughflow body. As a result, the throughflow body can be surrounded over a longer distance along the channel path by material of the element body and held on said element body.

Particularly when the fluid line element in fact comprises a throughflow body on the first but not on the second throughflow opening, said fluid line element can comprise, on the end region thereof which comprises in each case the respective other collar-less throughflow opening or is located closest to said collar-less throughflow opening, a recess which extends along the channel path in the direction into the element body and surrounds the channel path. Preferably, according to the present designs, the collar-less throughflow opening is the second throughflow opening, which can be free of a throughflow body.

The surrounding recess is formed for the introduction and the accommodation, at least in sections, of the protruding surrounding collar, as it was discussed above, of an additional, preferably identical fluid line element. Due to the introduction of the surrounding collar of the additional fluid element into the associated recess of another fluid element, the flow channels of the two fluid line elements can be connected collinearly in a particularly simple way without additional tool.

For this reason, according to a preferred development of the present invention, an inner peripheral surface section of the recess is formed as a complementary shape of an outer peripheral section of the protruding surrounding collar, so that two fluid line elements can be positively connected to one another with collinear flow channels via recess and collar with the least possible play.

Alternatively or additionally, the collinear connection of the flow channels of two fluid line elements directly adjacent along a now common channel path can also be achieved by using the throughflow body as a plug connection element. For this purpose, all that is needed is that the throughflow body of the fluid element according to the invention protrudes along the channel path of said fluid element beyond the element body thereof.

Therefore, it is advantageous if the fluid line element according to the invention comprises, on the end region thereof comprising the second throughflow opening or on the end region thereof located closest to the second throughflow opening, a depression extending along the channel path in the direction into the element body and surrounding the channel path. This depression can be formed for the introduction and the accommodation, at least in sections, of the throughflow body section protruding beyond the element body of the previously mentioned fluid line element.

Preferably, the depression of the fluid line element comprises a radial protrusion or a ledge with which the longitudinal end of the throughflow body protruding from it—longitudinal end which faces away from the element body of the additional fluid element—comes in contact, when the fluid line element is connected to the additional fluid line element. Indeed, in that case, the throughflow body of the additional element can also come in sealing contact on the radial protrusion of the fluid line element. Preferably, according to an advantageous development of the present invention, the depression can have dimensions such that, in the case of complete approach of fluid line element and additional fluid line element, the two radial protrusions, against which a longitudinal end of the throughflow body is braced in each case, the separation thereof along the common channel path is shorter than the length of the throughflow body along the channel path in the relaxed state. As a result, in the case of connection of fluid line element and additional fluid line element, the throughflow body can be prestressed by resilient deformation, as a result of which the sealing effect thereof on the connection site of the two fluid line elements with one another can be improved.

Moreover, in order to increase the sealing effect, an inner peripheral surface section of the depression can be designed as a complementary shape of an outer peripheral surface section of the protruding throughflow body section. In this case, it is possible that both the longitudinal ends and thus the end faces of the throughflow body, and also an outer peripheral surface section of same, surrounding the channel path, butt against the inner peripheral surface section of the depression and thus provide a good flow barring effect.

Naturally, in a particularly preferred embodiment example, both the surrounding recess and the depression are provided. For this purpose, it is possible to provide, in detail, that the surrounding recess comprises a first recess region located closer to an outer side of the element body, and a second recess region located farther from the outer side of the element body along the channel path in the direction into the element body, second recess region which has a smaller clear width than the first recess region, wherein the first recess region is designed for the introduction and the accommodation, at least in sections, of a protruding surrounding collar of an additional fluid line element, for the purpose of which preferably an inner peripheral surface section of the first recess region is formed as a complementary shape of an outer peripheral surface section of the protruding surrounding collar of an additional fluid line element, and wherein the second recess region is designed for the introduction and the accommodation, at least in sections, of a throughflow body section of the additional fluid line element, which protrudes beyond the element body, for the purpose of which preferably an inner peripheral surface section of the second recess region is formed as a complementary shape of an outer peripheral surface section of the protruding throughflow body section. In terms of function and construction, the second recess region here corresponds to the above-mentioned depression, so that the advantageous developments described for the depression also apply to the second recess region.

In order to generate as little flow loss in the fluid line element as possible, it is preferable that the first throughflow opening and the second throughflow opening are arranged coaxially along a straight channel path. Alternatively, the channel path extending between the first and the second throughflow openings can also be bent at a right angle. Admittedly, in that case, flow loss occurs at the site of the bend, but a channel path bent at a right angle nonetheless makes it possible to achieve a very good use of installation space for the formation of a fluid line section by means of the mentioned fluid line elements. The first and the second throughflow openings are arranged apart from one another in the channel path direction.

In some cases it can be necessary or helpful if a fluid line element enables the feeding or discharging of a fluid through an additional flow channel into or from the flow channel already present in the fluid line element. For this purpose, the fluid line element can be designed according to an advantageous development of the present invention in such a manner that at least one additional throughflow opening is provided along the channel path between the first and the second throughflow openings, into which a supplementary flow channel leads or which is run through by a supplementary flow channel, wherein the supplementary flow channel leads at an angle into the flow channel extending between the first and second throughflow openings. For the abovementioned reasons pertaining to good use of the installation space, the supplementary flow channel preferably leads at a right angle into the flow channel extending between the first and second throughflow openings. However, any other angle can also be selected if this would be advantageous for the respective desired individual flow course.

The present invention moreover relates to a fluid line arrangement having at least one fluid line element as it was described above. This at least one fluid line element, hereafter referred to as "first fluid line element," can be designed in accordance with the above-described advantageous developments.

In addition, the fluid line arrangement can be connected, for the targeted fluidic connection of the flow channel of the fluid line element to an additional fluid line element, referred to hereafter as "fluid line connection element." This fluid line connection element has the following features: an element base shape, a passage opening provided on the element base shape, and a throughflow channel which passes through the element base shape along a passage path, wherein, in the region of the throughflow channel, a magnet is provided, and wherein the fluid line connection element comprises a valve seat formation and an attachment formation for the attachment onto a supporting structure, in particular an attachment formation which can be snapped onto a counter-formation of the supporting structure.

Due to the valve seat formation, the throughflow channel of the fluid line connection element can be released or barred for throughflow by means of a suitable valve body. The magnet provided in the region of the throughflow channel here enables the use of a ferromagnetic valve body, so that a contact-less releasing or barring of the throughflow channel is possible, which is advantageous for ultraclean laboratory arrangements.

By means of the attachment formation, the fluid line connection element can be attached to a supporting structure. This can occur in a particularly advantageous and simple manner by snapping the attachment formation onto a corresponding counter-formation of the supporting structure, as a result of which the attachment formation is preferably designed as a snap-in attachment formation. In terms of construction, this can be implemented in a particularly simple manner, for example, by means of one or more spring-loaded protrusions.

The term "element base shape" is selected to distinguish it linguistically from the element body of the previously described fluid line element. In fact, the term "element base shape" refers to nothing other than an element body. The above-mentioned properties of an element body of a fluid line element therefore also apply to the fluid line connection element mentioned now in connection with the fluid line arrangement. The statements made above regarding the throughflow opening apply in the same way to the throughflow opening of the fluid line connection element, and the statements made above regarding the channel path also apply to the passage path of the fluid line connection element. Finally, the statements made above concerning the flow channel in the fluid line element apply to the throughflow channel of the fluid line connection element. The terms "passage opening," "passage path" and "throughflow channel" are selected essentially to distinguish them linguistically from the "throughflow opening," "channel path" and "flow channel," in order to make their assignment to the fluid line connection element also very clear linguistically. Repetitions of the description of these designs on the fluid line connection element are consequently omitted. Instead, reference is made to the description of the corresponding designs of the fluid line element.

The passage path of the fluid line connection element should be used subsequently just like the channel path of the fluid line element used before as reference section coordinate of the element, which defines an axial coordinate extending longitudinally along the path and a radial component extending away from the path or toward the path.

To facilitate the attachment and also the exchange of a valve body, it is advantageous to provide the valve seat formation on the fluid line connection element—relative to the passage path thereof—on a longitudinal end region thereof. In order to prevent said valve seat formation from being interfered with by the attachment to the above-mentioned supporting structure and to ensure moreover that the attachment of the fluid line connection element to the supporting structure can occur without risk of damage to or soiling of the valve seat formation, the attachment formation is provided advantageously on the respective opposite longitudinal end region of the fluid line connection element, which supports the valve seat formation.

The provision of the valve seat arrangement on a longitudinal end region of the fluid line connection element moreover also makes it possible to use a valve body arranged on the valve seat formation or held by the magnet on the fluid line connection element in a fluid line element fluidically connected to the fluid line connection element.

In order to be able to ensure the best possible sealing of the valve seat formation in the collaboration with a valve body resting thereon, the valve seat formation preferably comprises a flexible seat component. This seat component can be deformed by a valve body, which preferably comprises a ferromagnetic material or is formed from such a ferromagnetic material, under the action of the magnetic force generated in the interaction with the magnet, so that the flexible seat component is in nestling contact with the valve body sitting thereon.

In order to be able to generate the highest possible magnetic force with a small construction volume of the magnet, the magnet is preferably formed with the involvement of rare earths as undeformable solid body when used for the intended purpose. Therefore, the flexible seat component is preferably formed separately from the magnet. However, this should not rule out the use of a plastic filled with ferromagnetic particles as the magnet.

Since the element base shape, for stability reasons, is generally designed as a solid body which is an undeformable solid body when used for the intended purpose of the fluid line connection element, in comparison to the seat component, the flexible seat component of the valve seat formation is particularly preferably also formed separately from the element base shape. As flexible seat component, elastomer seat components can be considered, for example, using rubber and/or silicone.

Preferably, the throughflow body of the fluid line element and the flexible seat component of the valve seat formation are fabricated from the same material.

In a development of the provision of the valve seat formation on a longitudinal end region of the fluid line connection element, the valve seat formation, in particular the seat component, can form a longitudinal end of the fluid line connection element.

In order to arrange the magnet of the element base shape in a manner that reduces the installation space, and, in particular, to achieve the most even possible application of force in the collaboration with a valve body, it is preferable that the magnet comprises a passage opening through which flow can occur and which surrounds the throughflow channel. For reasons pertaining to simple fabrication and installation, it is preferable, in this context, that the magnet even forms a section of the throughflow channel, that is to say that it is wettable by the fluid which flows through the throughflow channel on at least the side of the magnet facing the throughflow channel. To achieve the most even possible application of force, the magnet is preferably designed in the form of a ring.

For the reliable attachment of the fluid line connection element to the supporting structure, it is possible to provide that the attachment formation comprises a collar, preferably a ring collar, with at least one snap-in protrusion which is radially resilient relative to the passage path or with a rigid snap-in protrusion that can be engaged from behind radially relative to the passage path, or with a snap-in recess that can be engaged from behind radially relative to the passage path.

The installation of the magnet can occur in a particularly simple manner when the magnet is inserted in a recess in the element base shape, which forms the flow channel, at least in sections. The magnet then forms a flow cross section reduction of the throughflow channel. A simple attachment of the magnet in the throughflow channel without tool can occur advantageously by snap-in connection. This can be implemented in terms of construction by a snap-in nose protruding radially in the throughflow channel with respect to the passage path. The snap-in nose can surround the passage path continuously. When lower latching forces are required, the snap-in nose can surround the passage path with interruptions or be provided only locally in a few peripheral sections, which are then preferably arranged equidistantly from one another in the peripheral direction around the passage path.

The valve body, which has already been mentioned above, can be part of the fluid line arrangement. Preferably the valve body rests, at least in an operating state of the fluid line arrangement, on the valve seat formation of the fluid line connection element. To provide the best possible sealing of the valve body sitting on the valve seat formation, the valve body is preferably formed as a valve ball.

The ferromagnetic material of the valve body can be permanently magnetized or it can be substantially unmagnetized and merely respond to the magnetic field of the magnet in the fluid line connection element.

The fluid line arrangement can comprise a second fluid line element, as it was described above. The second fluid line element can moreover comprise one or more of the above-mentioned developments of the fluid line element. The first fluid line element then preferably comprises a supplementary flow channel to which the throughflow channel of the fluid line connection element is preferably connected. In this case, the flow channel of the first fluid line element can be part of a fluid line section to which the flow channel of the second fluid line element also belongs, wherein, through the supplementary channel, by means of the throughflow channel of the fluid line connection element which can be closed with a valve body, fluid can be introduced in a targeted manner into the fluid line section formed with the involvement of the flow channels of the first and the second fluid line elements. The mentioned fluid line elements and the fluid line connection element can therefore be coupled to one another in such a manner that the second throughflow opening of the first fluid line element is coupled to the first throughflow opening of the second fluid line element, in order to connect the flow channels of the first and the second fluid line elements to one another in series, wherein the fluid line connection element is coupled with the longitudinal end thereof located closest to the valve seat formation to the additional throughflow opening of the first fluid line element, in order to connect the throughflow channel of the fluid line connection element to the supplementary flow channel of the first fluid line element in series.

When the fluid line connection element comprises the above-mentioned flexible seat component, it can be used not only for the sealing with a valve body but also for the sealing against the first fluid line element, if the flexible seat component comprises a seat section which is designed to butt against a valve body and which moreover comprises the sealing section which, on the one hand, butts against the element base shape of the fluid line connection element and, on the other hand, against the element body of the first fluid line element.

Preferably, the seat component surrounds the throughflow channel, in order to provide, continuously in the peripheral direction, a sealing with respect to the fluid line element.

The above-mentioned fluid line elements (including the fluid line connection element) enable a very flexible formation of a fluid line arrangement with any desired number of feed lines and discharge lines. For example, the second fluid line element can also comprise a supplementary flow channel which can be connected to the throughflow channel of an additional fluid line connection element, as it was described above, to form a common channel. This second fluid line element in turn can be connected to an additional fluid line element, as described above and preferably developed further, and, in particular, in that the second throughflow opening thereof is coupled to the first throughflow opening of the additional fluid line element. As a result, the flow channels of the second and of the additional fluid line element can be connected to one another in series, so that a fluid line section can be formed with involvement of the flow channels of the first, of the second and of the additional fluid line element. This fluid line section is preferably straight. The supplementary flow channels of the fluid line elements can lead into it and thus produce feed and/or discharge connections. The additional fluid line connection element is then coupled, as already indicated above, to the additional throughflow opening of the second fluid line element.

As already described above, the fluid line connection element and/or the additional fluid line connection element can comprise a valve body comprising ferromagnetic and preferably made from ferromagnetic material, which rests, in an operating state, on the respective valve seat formation. Said valve body in turn is preferably a valve ball.

The valve body can then be located in a movement space which is formed, at least in sections, from flow channel and supplementary flow channel of the first fluid line element as well as from a section of the throughflow channel of the fluid line connection element, or which is formed, at least in sections, from flow channel and supplementary flow channel of the second fluid line element as well as from a section of the throughflow channel of the additional fluid line connection element. The longitudinal ends—which face the respective movement space—of the throughflow bodies of the fluid line elements involved in the formation of the movement space advantageously comprise the above-mentioned valve seat formations, so that these longitudinal ends of the throughflow body(ies) can also be used as valve seats. In this way, by means of a valve body, different flow paths through the fluid line arrangement can be implemented, in particular by contactless switching by means of magnetic forces from outside of the fluid line arrangement.

The present invention therefore also relates to a valve line arrangement with a fluid line arrangement designed as described above, which moreover comprises a switching arrangement. The switching arrangement is used in order to switch the valve body in the fluid line connection element made, at least in sections, of channels of a fluid line element and of a fluid line connection element connected thereto, between different valve body positions. To make it possible to switch the valve body in a contactless manner between different positions, the switching arrangement, in a switching region of the movement space, switching region which is located closer to the valve seat formation associated with it of the throughflow body of the first fluid line element than to the valve seat formation of the fluid line connection element, and/or in a switching region of the movement space, switching region which is located closer to an additional valve seat formation associated with it of the throughflow body of the second fluid line element than to the valve seat formation of the fluid line connection element, is designed to provide a magnetic field which can be varied with regard to the magnetic field strength acting locally in the switching region, in order to shift the valve element from the contact with the valve seat construct to the contact with the valve seat construct associated with the respective switching region by varying the magnetic field strength.

The assignment of a valve seat formation to a switching region occurs due to the spatial proximity of the switching region to the valve seat formation. The switching region, in which the magnetic field with variable magnetic field strength can be provided, can be identified by the means providing the magnetic field. This means can be an electromagnet, for example, which can be supplied with various current levels in order to vary the magnetic field strength of the magnetic field originating therefrom depending on desired switching states. This includes an operating state with electromagnets that are not supplied with current. In this case, the electromagnet will be located closer to the valve seat formation associated with it than to the valve seat formation not associated with it of the same movement space.

However, the use of electromagnets as a means providing a variable magnetic field is not preferable, since the different levels of energization states of the electromagnet can lead to heat development in the surroundings of the electromagnet. As a result, heat energy coming from the electromagnets can be transmitted to a fluid flowing in the channels of the fluid line arrangement, which can lead to an undesirable heating of the fluid. Therefore, thermally sensitive fluids, which must have a nominal operating temperature with a tolerance of only ±0.5 K, are run through the channels of the fluid line arrangement.

Therefore, in order to avoid any undesired heating of the fluid due to the use of electromagnets, it is preferable that the switching arrangement comprises at least one permanent magnet which can be moved closer to or father from the first fluid line element, in particular to a valve seat formation of same, along a switching movement path, or farther from said first fluid line element.

By moving the permanent magnet closer to the associated valve seat formation or farther from it, a magnetic field that is variable locally in the switching region can also be provided.

The switching movement path is preferably orthogonal to the channel path on the valve seat formation associated with the permanent magnet. A correct seating of the valve body on the valve seat formation associated with a magnet for the generation of a variable magnetic field can be achieved by appropriate dimensioning of the flow channel, in spite of the possibly asymmetric arrangement of the magnet with respect to the channel path section passing through the valve seat formation. When the flow channel has a clear width orthogonally with respect to the channel path, at least in the vicinity of the valve seat formation, width which is only insignificantly greater than the dimension of the valve body to be measured in the same direction, the valve body can be moved without excessive friction losses through the variable magnetic field of the magnet associated with the valve seat formation toward the valve seat formation, without deviating excessively from the preferably central position thereof relative to the channel path. For this reason as well, the use of a valve ball as valve body is preferable, since this valve ball always has the same dimensions on all sides, independently of the local orientation thereof. As flow channel, a cylindrical flow channel can be used.

A reliable contact of the valve body on the valve seat formation associated with the permanent magnet can be achieved in that the imaginary straight extension of the switching movement path into the element body of the first fluid line element either passes either through the throughflow body associated with the switching region, or—viewing the valve body abutting against the valve seat formation—through the movement space between the valve seat formation associated with the switching region and the valve body section having the largest dimension orthogonally with respect to the channel path. In this case, even in the case of a switching movement path extending orthogonally with respect to the channel path, there always remains a magnetic force coming from the permanent magnet acting on the valve body, magnetic force which has a force component that acts along the channel path towards the valve seat formation. In this way, when the permanent magnet is approached, the valve body is always exposed to a sufficient force axially in the direction toward the valve seat formation.

The permanent magnet can be driven in any desired manner for the approach to the channel path or for the removal from said channel path. In this context, spindle drives or similar electromechanical drives are conceivable. However, such electromechanical drives may not be suitable for the generation of particularly brief switching times. In addition, magnetic fields can originate from them in turn. Finally, these drives can also act undesirably as heat source.

Therefore, the permanent magnet that can be moved closer and removed again is preferably driven by a piston-cylinder arrangement, wherein, for the joint movement, in the case of a cylinder firmly attached to a supporting structure, the permanent magnet can be coupled to the piston rod, or, in the case of a piston rod firmly connected to a supporting structure, can be coupled to the cylinder. As working fluid of the piston-cylinder arrangement, one can consider using fluids such as, for example, hydraulic oil, or a gas, in particular air. The switching movement drive of the permanent magnet is preferably pneumatic. The piston-cylinder arrangement can work for resetting against the resilient force of a resetting spring, which prestresses the permanent magnet into an operating position. Then, for the duration of a valve switching position acting on the fluid line arrangement, the pressure in the piston-cylinder arrangement against the action of the resetting spring needs to be maintained. Alternatively, a piston-cylinder arrangement with double-acting cylinder can be used. Then, a pressure impact can be sufficient for the generation of a desired switching movement of the at least one permanent magnet.

When the throughflow body associated with the switching region has both a valve seat formation and an additional valve seat formation, the imaginary extension of the switching movement path passes through the throughflow body or the movement space closer to the valve seat formation associated with the switching region than to the respective other valve seat formation. As a result, it is possible to prevent unintentionally causing the incorrect valve body to butt against a valve seat formation of a throughflow body.

As described above, the fluid line arrangement can comprise several movement spaces each with a valve body. For example, for each fluid line connection element, a separate movement space with its own valve body can be formed. Then, for the targeted switching of the different valve bodies, at least one permanent magnet is provided for each movement space, permanent magnet which in each case can be moved closer to each fluid line element or removed therefrom, the flow channel and supplementary flow channel thereof contributing to the formation of the respective movement space.

If a movement space comprises several valve seat formations, for example, via a valve seat formation of the throughflow body of the first fluid line element and via an additional valve seat formation of the throughflow body of the second fluid line element coupled to the first fluid line element, then, for each valve seat formation facing the movement space and associated therewith, a permanent magnet which can be moved closer to the fluid line element or removed therefrom can be provided. Then, a permanent magnet which can be moved closer or removed is then preferably associated with each valve seat formation.

The present invention moreover relates to a handling device having a valve line arrangement designed as described above. The handling device moreover comprises a supporting structure accommodating the valve line arrangement, a plurality of supply lines leading toward and/or away from the valve line arrangement, wherein at least some of the supply lines, preferably all the supply lines, in each case comprise a line section which is formed by a throughflow channel of a fluid line connection element, and a connection throughflow opening which is formed for the detachable, temporary connection of a laboratory vessel or of a fluid line leading to a laboratory vessel, wherein the plurality of fluid line connecting elements is fluidically connected by means of a plurality of fluid line elements to the connection throughflow opening or can be fluidically connected by means of the switching arrangement.

By means of the handling device, the same valve line arrangement can be coupled to different laboratory vessels such as, for example, cell culture vessels, in a fluid-transmitting manner. In this way, a plurality of laboratory vessels can be processed by means of a single handling device with regard to fluid introduction and fluid discharge.

In another aspect, the present invention relates generally to a handling device with a valve line arrangement, in particular for a cell culture installation, for the introduction of a fluid into a laboratory vessel, in particular a cell culture vessel, and/or for the discharge of a fluid therefrom, and with a supporting structure accommodating the valve line arrangement, the valve line arrangement comprising a line component with a first coupling formation for the temporary coupling of a first fluid channel, preferably of a fluid channel of a laboratory vessel, with a second coupling formation for the temporary or permanent coupling of a second fluid channel, preferably of a fluid channel for a fluid reservoir, and with a third coupling formation for the temporary or permanent coupling of a third fluid channel, preferably of a discharge channel, coupling formations which in each case are run through by a fluid line section, wherein, in the line component, a flow channel arrangement is formed, by means of which in each fluid line section of the first, the second and the third coupling formation is or can be connected to at least one fluid line section of one of the other two coupling formations for the fluid transport.

Preferably, each fluid line section of the first, the second and the third coupling formation is or can be connected to each fluid line section of the other two coupling formations for the fluid transport.

According to this aspect of the present invention, line component should be understood to mean a component formed as a physical component. This component can be designed, for example, as an above-described fluid line arrangement with at least one fluid line element and with a plurality of fluid line connection elements. In such a line component, a first coupling formation can be provided on a fluid line element, while two fluid line connection elements can be at least part of a second or third coupling formation. However, it should be pointed out explicitly that the line component is not limited to the above-described fluid line arrangement. The line component can, in addition, be formed by a plurality of subcomponents, when the complexity of the flow channel arrangement requires this.

In contrast to the line component, the flow channel arrangement does not refer to a component that is formed as a physical component, but only to a channel course between the three above-defined coupling formations. Consequently, in terms of the design thereof, there are no limitations in principle. For example, a flow channel arrangement formed by a plurality of flexible tubes or from assembled half shells or partial shells is also conceivable. In the case of a line component designed as a fluid line arrangement, the above-described flow channel and the supplementary flow channel form a part of the flow channel arrangement, which is defined by at least one fluid line element as a component in the form of a physical component.

In a development of the invention, it can be provided that the valve line arrangement comprises a fluid channel support which is movable relative to the line component and comprises at least two fluid channel support connection formations formed separately from one another and connected to different fluid channels for the fluid transport, and which in each case are run through by a fluid channel section, and wherein at least one of the three coupling formations is designed as an exchange coupling formation for the temporary establishment of a common fluid line section with a fluid channel support connection formation that can be selected by means of a relative movement of line component and fluid channel support.

In this design, the fluid channel support comprises at least two fluid channel support connection formations designed separately from one another and connected to different fluid channels for the fluid transport, each of which can be temporarily coupled for the establishment of a common fluid line section to the exchange coupling formation of the line component. The fluid channel support connection formation, which is intended to form, together with the exchange coupling formation of the line component, a common fluid line section, can be selected in a simple manner by relative movement of fluid channel support and line component. In this way, advantageously, a large number of fluid channels leading to and/or away from the valve line arrangement can be connected permanently to the valve line arrangement, and provided as coupling formations on the line component. Thus, coupling formations on the line component can be omitted, which in turn leads to a reduction of installation space.

The different coupling formations provided on the line component, and the flow channel arrangement connecting said coupling formations should be able to provide different fluid line sections for different fluids to increase operational hygiene. Advantageously, this can occur in that a plurality of coupling formations, preferably all the coupling formations, with the exception of the coupling formation for the temporary coupling of a fluid channel of a laboratory vessel, comprise(s) a valve seat and a valve body, wherein, in an operating state with a fluid line section of a coupling formation that is barred to fluid passage, the valve body rests on the valve seat.

In this context, in a particularly preferred embodiment, it is also possible to provide that, in the flow channel arrangement, apart from the coupling formations, a valve seat and a valve body are provided for the fluidic separation of different regions of the flow channel arrangement, wherein, in an operating state with regions of the flow channel arrangement that are fluidically separated from each other, the valve body rests on the valve seat.

In terms of construction, this development can be implemented in that the valve body is formed at least partially, preferably entirely, from ferromagnetic material, and in that the valve seat comprises a magnet which prestresses the valve body magnetically into a closed position in which the valve body rests on the valve seat. For the most homogeneous force distribution possible in the prestressing of the valve body toward the valve seat, it can be advantageous to use an annular magnet. Preferably, the magnet which prestresses the valve body into the closed position can have a fluid flow through it, so that it can be provided, with small installation space requirement, in or close to the coupling formation comprising the valve seat.

A particularly advantageous possibility for switching the valve body in a contactless and thus very hygienic manner between two positions, in one of which the valve body bars fluid passage through the valve seat, and, in the other, enables the fluid passage through the valve seat, can be implemented in that the valve body comprises ferromagnetic material, in particular, it is manufactured from ferromagnetic material, and in that the valve line arrangement comprises a switching arrangement with a magnetic field strength which can be varied locally on the coupling formations, and by means of which the valve body can be detached from the valve seat.

If a valve body is provided to butt against several valve seats, it can be sufficient that only one of these valve seats comprises a magnet. The valve body can be held in contact with the other valve seats temporarily by the switching arrangement.

Each of the above-described handling devices can comprise, for the coupling of the laboratory vessel to the valve line arrangement, a moving part such as, for example, a carriage or cart. The moving part is designed for the temporary accommodation of a laboratory vessel, and it can be moved closer to or farther from the valve line arrangement along a connection path. By means of the moving part, the laboratory vessel accommodated thereon can be guided reliably and thus coupled with high operational security to the valve line arrangement, in particular to the connection throughflow opening, and uncoupled again from it.

In particular, when cell culture vessels are used as laboratory vessels, it can be desirable that the inner surfaces of the laboratory vessel are wetted with a fluid introduced into the laboratory vessel. For this purpose, it is possible to provide that the moving part and the valve line arrangement are provided, at least when the moving part is in a position moved closer to the valve line arrangement, so that they can be pivoted around a common pivot axis, which extends preferably orthogonally to the connection path, on a supporting frame of the handling device. In this manner, via the valve line arrangement, a liquid, for example, a nutrient liquid for cell cultures, can be introduced in the cell culture vessel, wherein the laboratory vessel can be pivoted immediately after the introduction of the liquid, while still coupled to the valve line arrangement, around the pivot axis, in order to achieve a targeted wetting of inner surfaces of the laboratory vessel with the liquid introduced.

As pivot drive, an electric motor drive can be provided, which is set up in order to transmit a driving force to a pivot shaft coupled to the supporting frame for the common pivoting movement. A simple and compact construction can be provided in that the pivot drive comprises a belt which extends around a pulley connected in a rotationally fixed manner to the pivot shaft, and/or a gear drive. Alternatively, it is also possible that the pivot drive is coupled directly to the pivot shaft or is the pivot shaft. In addition, designs are also conceivable in which no pivot shaft is provided, instead, for example, only a gear wheel connected in a rotationally fixed manner to the moving part is provided, gear wheel to which the pivot drive can transmit a drive force.

Figure 2:
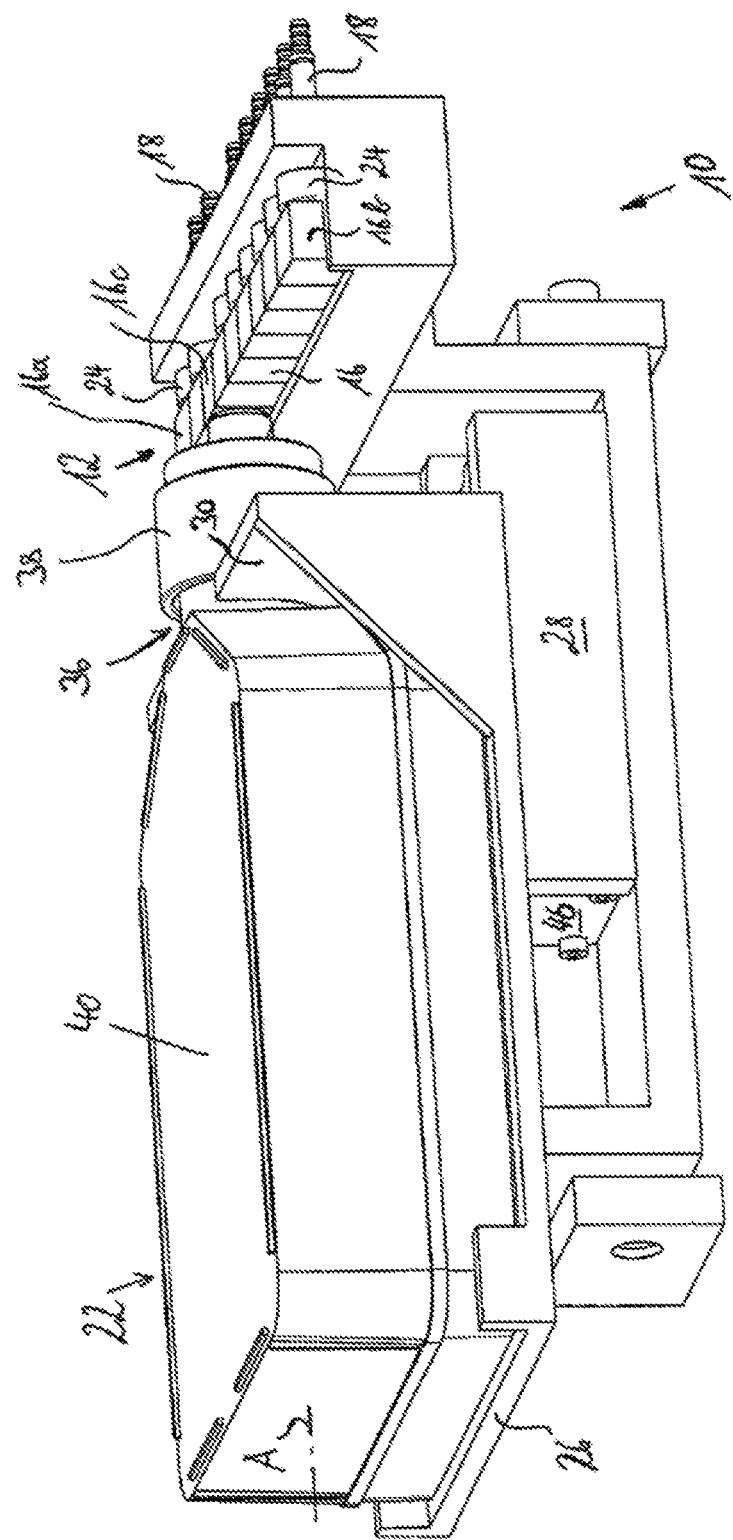
Figure 3:
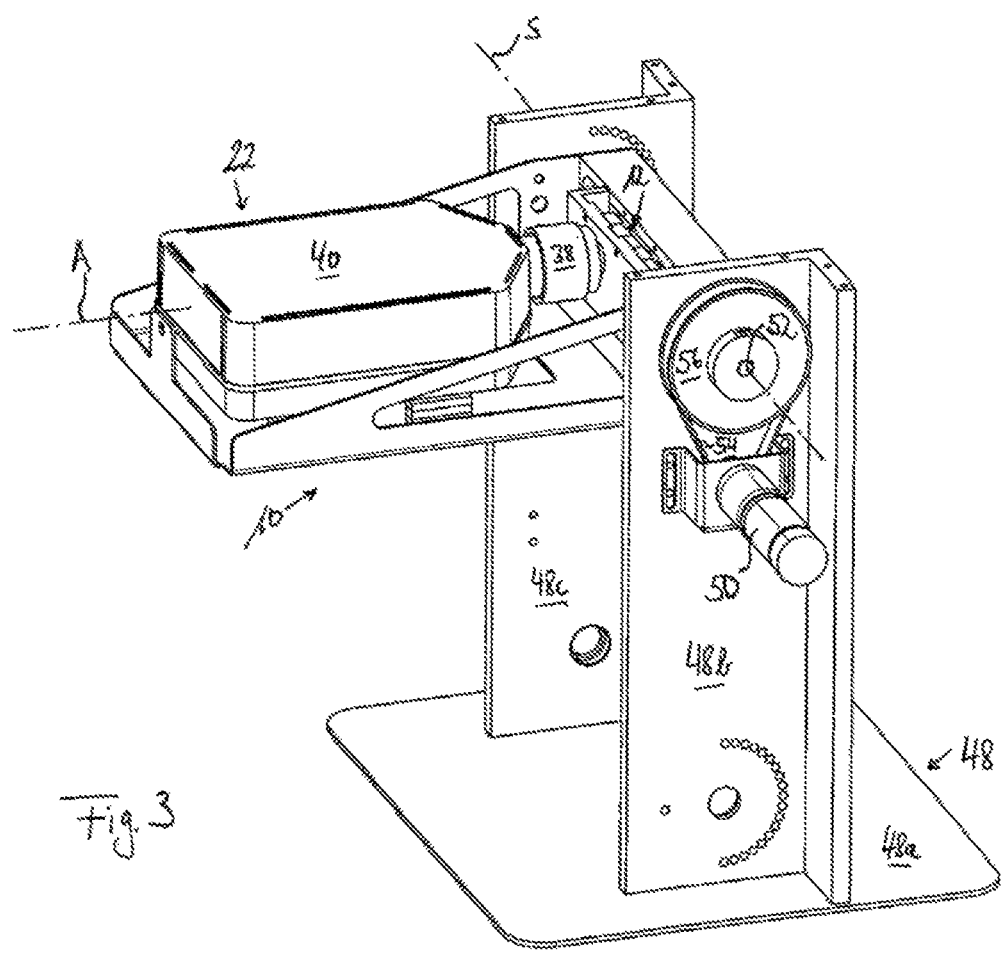
Figure 10:
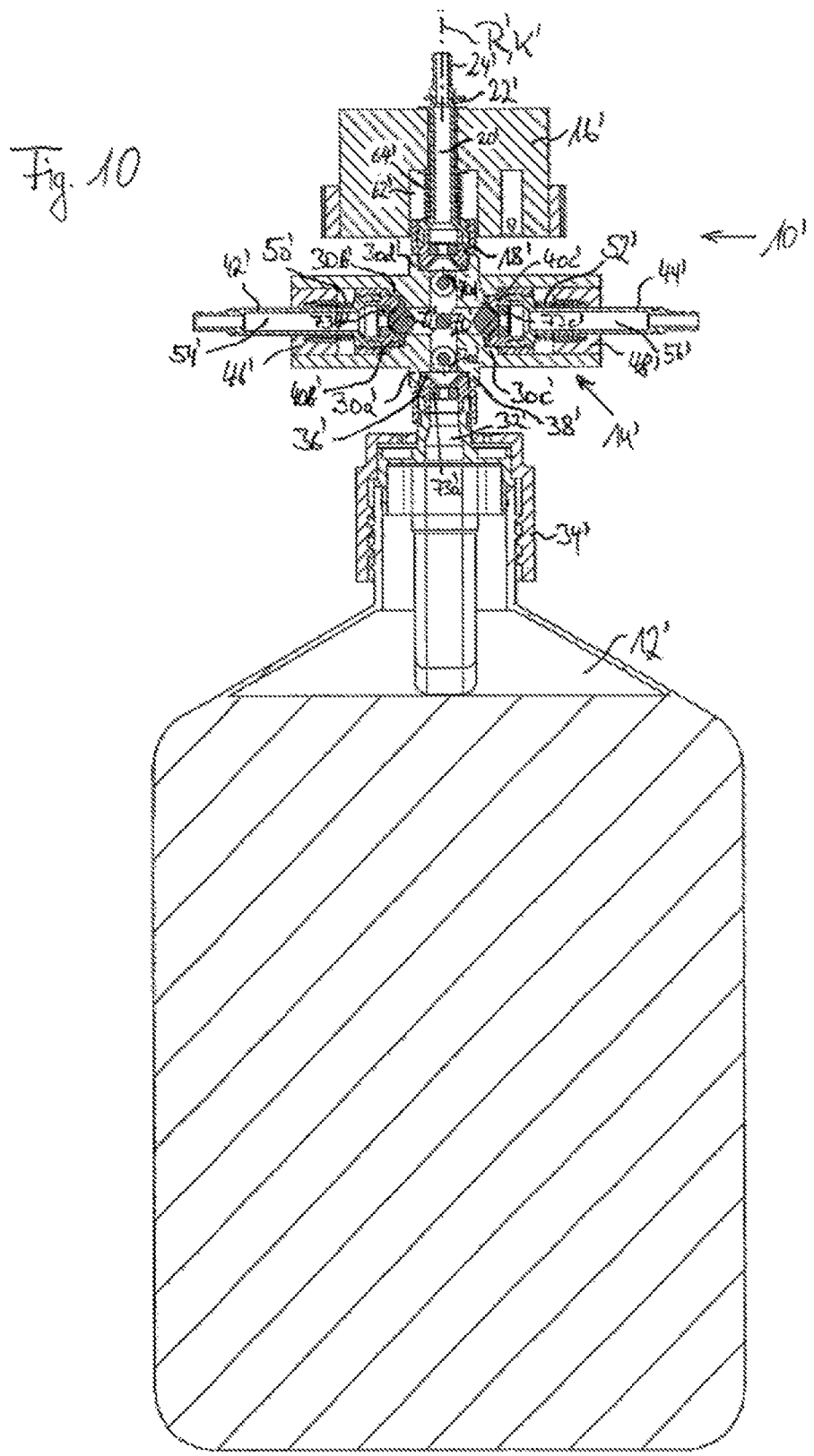

The present invention is described in greater detail below in reference to the appended drawings. The drawings show:

FIG. 1 a perspective view of a part of a handling device according to the invention, FIG. 2 the part of the handling device of FIG. 1 in an operating state with a laboratory vessel coupled to a fluid line arrangement, FIG. 3 a handling device according to the invention with the setup part already represented in FIGS. 1 and 2, FIG. 4 the handling device of FIG. 3 in an additional operating state, FIG. 5*a* a cross-sectional view through the valve line arrangement of FIG. 8 along the section plane Va-Va in FIG. 8, the valve line arrangement comprises the fluid line arrangement of the handling device of FIGS. 1 to 4, FIG. 5*b* an enlarged representation of a detail of the sectional view of FIG. 5*a*, but with valve bodies butting against the valve seat formations of the fluid line connection elements, corresponding to the operating state of FIG. 7, FIG. 6 a perspective view of the valve line arrangement of the handling device of FIG. 2 (with coupled laboratory vessel), FIG. 7 a longitudinal sectional view through the valve line arrangement of FIG. 6, viewed in the direction toward the laboratory vessel, FIG. 8 a sectional view of the valve line arrangement of FIG. 5*a* along the section plane VIII-VIII of FIG. 5*a*; the view of FIG. 8 also corresponds to the longitudinal sectional view of FIG. 7, but with another operating state of the valve line arrangement, FIG. 9 a perspective view of part of a second embodiment of a handling device according to the invention, and FIG. 10 a longitudinal sectional view through the part of the handling device according to the second embodiment, shown in FIG. 9.

In FIGS. 1 and 2, a supporting structure is marked in general with 10. In the supporting structure, a valve line arrangement can be accommodated, of which only the fluid line arrangement 12 is represented in FIGS. 1 and 2. A switching arrangement 14 which also belongs to the valve line arrangement is represented in FIGS. 6 to 8.

The fluid line arrangement 12 comprises a plurality of fluid line elements 16 which are fluidically connected to one another. The fluid line elements 16 which, in the represented fluid line arrangement, are not end-side fluid line elements 16*a* or 16*b* can each comprise a flow channel, not represented in FIGS. 1 and 2, and a supplementary channel branching off therefrom at a right angle. At another throughflow opening of the fluid line elements 16, by means of which the respective supplementary flow channels of the individual fluid line elements 16 are open to the outside environment of the fluid line elements 16, connecting pieces 18 can be provided, to which fluid lines can be connected, which can connect the respective fluid line element 16 and thus the fluid line arrangement 12 to fluid reservoirs or waste containers ("waste").

A fluid line element 16c is arranged in the fluid line arrangement 12 so that it is oriented in such a manner that the additional throughflow opening thereof leads to a laboratory vessel accommodation 20, on which a laboratory vessel 22 can be accommodated.

The fluid line elements 16 can be fluidically connected to the connecting piece 18 by means of fluid line connection elements 24. The fluid line arrangement 12 with the fluid line elements 16 and the fluid line connection elements 24 is explained in further detail below in connection with FIGS. 5, 7 and 8.

The laboratory vessel accommodation 20 can comprise a moving part 26, on which the laboratory vessel 22 can be accommodated temporarily. The moving part 26, here preferably in the form of a carriage, can be connected via a linear guide 28 to the rest of the fixed supporting structure 10, in such a manner that the moving part 26 and with it the laboratory vessel 22 accommodated thereon can be brought closer to the fluid line arrangement 12 along an approach path A or removed again from said fluid line arrangement.

As positioning aid, and in order to ensure a transmission of force between the moving part 26 and laboratory vessel 22 accommodated thereon, the moving part 26 comprises an end wall 30 which is preferably oriented orthogonally with respect to the approach path A and in which a recess 32 can be formed, into which a section of the laboratory vessel can then engage, when said laboratory vessel is accommodated temporarily on the moving part 26. The recess 32 is used preferably for the temporary accommodation of a neck section 34 of a vessel neck 36 which is exposed in a region between a vessel cap 38 screwed onto the vessel neck 36, and a vessel body 40.

When the laboratory vessel 22 is accommodated on the moving part 26, the end wall 30 engages, with positive connection in the example shown, between vessel body 40 and vessel cap 38 with the exposed vessel neck section 34, so that the laboratory vessel 22 engages orthogonally with respect to the approach path (with the exception of a direction for lifting from the recess 32), as well as in both directions along the approach path A, in the end wall 30 of the moving part 26.

On the longitudinal end facing away from the vessel body 40, the vessel cap 38 comprises a valve arrangement 42 which can be fluidically coupled with the additional throughflow opening 44 of the fluid line element 16c to the fluid line arrangement 12, by approaching the laboratory vessel 22.

In the sense of the present application, a connection is then established "fluidically," if it allows the passage of fluid in principle. However, this should not exclude that operating states of this connection exist, in which a valve body prevents fluid passage through the fluidic connection.

The linear guide 28 is preferably coupled to a linear drive 46, which ensures the driving of the moving part 26 relative to the remaining supporting structure 10 along the approach path A. The linear drive 46, which is preferably integrated in the linear guide, is connected to a control apparatus, not represented in FIG. 1, which enables an actuation of the linear drive 46 for moving the moving part 20.

In FIGS. 3 and 4, the handling device of FIGS. 1 and 2 is represented with additional components, wherein, however, other components shown in FIGS. 1 and 2 are omitted for the sake of clarity. Thus, for example, FIGS. 3 and 4 show no moving part 26.

In FIGS. 3 and 4 a supporting frame 48 is represented, on which the supporting structure 10 of FIGS. 1 and 2 is attached in a pivotal manner around a pivot axis S. The supporting frame can comprise a base plate 48a, from which two supports 48b and 48c that are spaced from one another can protrude. The supports 48b and 48c hold the supporting structure known from FIGS. 1 and 2 between themselves in a manner so that they can pivot around the pivot axis S.

As pivot drive of the supporting structure 10, an electric motor drive 50 can be provided, which transmits its drive force in a suitable manner to a pivot shaft 52 which is coupled to the supporting structure 10 for the common pivoting movement. In the example represented in FIGS. 3 and 4, the pivot transmission occurs by means of a belt 54, which extends around a pulley 56 connected in a rotationally fixed manner to the pivot shaft 52. It is only for the sake of completeness that it is pointed out that the movement transmission can also occur by means of other suitable transmission means such as, for example, a gear drive. It is also conceivable that the driveshaft of the drive 50 is coupled directly to the pivot shaft 52 or is the pivot shaft 52.

FIGS. 3 and 4 represent different operating positions of the handling device showing that the supporting structure 10 in both figures is in a different relative pivot motion with respect to the supporting frame 48. This is used to facilitate the wetting of inner walls of the laboratory vessel 22, in particular of the vessel body 40 thereof, with a liquid filled into the laboratory vessel 22. Thus, after the laboratory vessel 22 has been moved closer to the fluid line arrangement 12 and thus after a fluidic connection has been established between the fluid line arrangement 12 and the laboratory vessel 22 by means of the valve arrangement 42 provided in the vessel cap 38, in a first operating position of the handling device, for example, the operating position of FIG. 3, via the above-explained connecting pieces and a suitable valve switching (this is explained further below), a fluid can be introduced into the laboratory vessel 22. Due to the force of gravity, immediately after the introduction with unchanged operating position—at the time of the introduction in the operating position shown in FIG. 3—, this fluid rests on the inner wall of the end side of the vessel body 40 which is located closer to the base plate 48a of the support frame 48.

By pivoting the laboratory vessel 22 around the pivot axis S, the fluid introduced into the laboratory vessel 22 can also be brought in contact with other inner surfaces of the laboratory vessel 22, which is advantageous, in particular, for cell culturing in the cell culture vessel which is represented as the laboratory vessel 22 both as an example and as preferable.

The laboratory vessel 22 is preferably a cell culture vessel for culturing adhering cells.

Below, particularly in reference to FIGS. 5a and 5b, the structure of the fluid line arrangement will be explained:

FIGS. 5a and 5b show a series of fluid line elements 16 which are fluidically coupled to one another and, in each case, to a fluid line connection element 24. The fluid line elements 16 and the fluid line connection elements 24 are fixed by means of a supporting structure, from which a supporting structure part 10a on the fluid element side, and a supporting structure part 10*b* on the fluid line connection element side are represented. The identical fluid line elements 16 shown in FIGS. 5*a* and 5*b* have the following structure:

In an element body 60, a preferably cylindrical flow channel 62 passing through the element body 60 is formed, which extends along a channel path K between a first throughflow opening 64 and a second throughflow opening 66.

In a first region 68 of the fluid line element 16, which is located closer to the first than to the second throughflow opening, a throughflow body 70 is provided, which forms a part of the flow channel 62. The throughflow body 70 is made of a material which has a lower elasticity modulus than the material of the element body 60, so that the throughflow body 70, when an external force is exerted on it, is deformed to a greater extent than the element body 60, which is optionally as rigid as possible. On the longitudinal end 70*a* thereof, which faces the interior of the element body 60, the throughflow body 70 comprises a valve seat formation 72, for example, in the form of a conical depression. A valve body 74 can be in matching contact with said valve seat formation and, in the operating situation shown in FIG. 5, it rests on a valve seat formation 76 of a seat component 78.

To be able to use the throughflow body 70 also on the fluid line element, adjacent in FIG. 5*b* on the left to the explained fluid line element 16 along the channel path K, as valve seat, an additional valve seat formation 80 is also formed on the longitudinal end 70*b* of the throughflow body 70 facing the outside environment of the fluid line element 16. Preferably, the throughflow body 70 is mirror symmetric with respect to a symmetry plane orthogonal to the channel path K and designed rotationally symmetrical with respect to the channel path K as rotation symmetry axis.

The throughflow body 70 is preferably formed from an elastomer material, for example, from a rubber material and/or a silicone material. The element body 60, on the other hand, is preferably formed from a thermoplastic plastic such as, for example, polypropylene, polyethylene or from polymethyl methacrylate. Other plastics can also be considered.

To facilitate the connection of the fluid line element 16 to an adjacent fluid line element, the fluid line element 16 shown as an example in FIG. 5 comprises, in the region of the first throughflow opening 64 thereof, a ring collar 82 which protrudes from the rest of the element body 60 along the channel path K and advantageously surrounds the throughflow body 70. As a result, on the one hand, a positioning aid for the relative positioning of two axially adjacent fluid line elements 16 can be formed, and, on the other hand, the retention of the throughflow body 70 on the element body 60 can be improved by increasing the contact surface between the material of the element body 60 and the throughflow body 70.

The throughflow body 70 butts with the longitudinal end 70*a* thereof against a radial ledge 84 of the element body 60, which extends preferably completely around the channel path K. In this manner, the throughflow body 70 is unequivocally positioned axially relative to the channel path with respect to the channel path relative to the element body 60.

In the region of the second throughflow opening 66, the element body 60 can comprise a depression 86 extending along the channel path K into the element body 60.

In the represented example, the depression 86 comprises a first accommodation region 86*a* located closer to the outer side of the element body 60 and which is suitable for the accommodation of a ring collar 82 of an adjacent fluid line element 16, in order to position said fluid line element relative to the fluid line element 16 with respect to the channel path K. Preferably, the inner peripheral surface of the first recess region 86*a* comprises a complementary shape with regard to an outer peripheral surface of a ring collar of an adjacent identical fluid line element 16, so that two fluid line elements 16, as a result of assembly, more precisely: as a result of the introduction of the ring collar 82 into the first recess region 86*a* of the fluid line element 16, can be connected to collinear channel paths K in such a manner that the two flow channels 62 thereof form a common long flow channel.

The depression 86 can moreover comprise a second recess region 86*b*, which is located farther from the outer side of the element body 60 in the direction into the element body 60. This second accommodation region 86*b* is used for the accommodation of an axially projecting longitudinal end 70*b* of an adjacent fluid line element 16, in order to connect two fluid line elements 16 in a fluid-tight manner to one another. For this purpose, the second recess region 86*b* can comprise a radial protrusion 88, against which an end side of the throughflow body 70 projecting from the adjacent fluid line element 16 butts in the finished installed state.

Thus, in the finished installed state of the fluid line arrangement 22, a throughflow body 70 abuts with the two opposite end sides thereof against two opposite radial protrusions 84 and 88, which are formed on two different fluid line elements 16.

Preferably, the depression 86, in particular the second recess region 86*b* thereof with the radial protrusion 88, and the radial protrusion 84 are arranged in such a manner that, in the finished installed state, they are at a smaller distance from one another than the dimension of the throughflow body 70 along the channel path in the unstressed states. When the fluid line arrangement 12 is installed, a slight axial compression of the throughflow body 70 therefore occurs, between the radial protrusions 84 and 88 associated therewith, which increases the sealing of the connection between two axially adjacent fluid line elements 16 formed with participation of the throughflow body 70.

It should be added that the inner peripheral surface of the second recess region 86*b* is formed to be complementary to the outer peripheral surface of the projecting longitudinal end region of a throughflow body 70, so that the outer peripheral area of the projecting section of a throughflow body 70 also butts, after introduction into the second recess region 86*b* of an adjacent fluid line element 16, against the outer peripheral surface thereof in the second recess region 86*b*, which in turn improves the sealing effect of the throughflow body 70.

Since, the throughflow body 70 associated with a fluid line element 16 is in contact with the associated element body 60 in the region of the first throughflow opening over a substantially larger contact surface than with the inner peripheral surface of an adjacent fluid line element, the throughflow body 70 remains in the fluid line element 16 associated with it when the fluid line arrangement 12 is dismantled.

The fluid line elements 16 shown in FIGS. 5*a* and 5*b* show, in addition to the flow channel 62, a supplementary flow channel 90 branching off therefrom. The latter leads into an additional throughflow opening 92. Preferably, the supplementary flow channel 90 is straight and branches at a right angle from the flow channel 62 used.

To the additional throughflow opening 72, a fluid line connection element 24 can be connected, which is preferably held on the supporting structure part 10b.

The fluid line connection element 24 comprises an element base shape 94, which is run through by a throughflow channel 96 along a throughflow path D.

By means of an attachment formation 98, designed preferably as a peripheral snap-in protrusion protruding radially inward toward the passage path D and radially resilient, the fluid connection element is fixed by snap-in connection to a counter-formation 100 of the supporting structure 10, more precisely: of the supporting structure part 10b.

The attachment formation 98 is formed on a longitudinal end of the fluid line connection element 24.

On the longitudinal end opposite the former longitudinal end, according to a preferred embodiment of the present invention, the above-mentioned elastomer seat component 78 with the valve seat formation 76 is arranged. The seat component 78 thus preferably forms a longitudinal end of the fluid line connection element 24 in the preferred embodiment example represented.

In addition to the valve seat formation 76, the seat component 78 comprises a sealing section 102 which preferably surrounds the valve seat formation 76, or the seat section 77 of the seat component 78 comprising the valve seat formation 76, radially externally. In the finished installed state, the sealing section 102 is preferably clamped between a section of the element body 60 surrounding the additional throughflow opening 92, and a section of the element base shape 94 surrounding the throughflow channel 96, in order to seal the connection between the supplementary flow channel 90 of the fluid line element 16 and the flow channel 96 of the fluid line connection element 24.

The fluid connection element 24 comprises moreover a permanent magnet 104, which preferably surrounds a part of the throughflow channel, and particularly preferably forms a part thereof.

In the example represented here, the permanent magnet 104 is pushed from the longitudinal end of the throughflow channel 96, which is located closer to the attachment formation 98, into said throughflow channel along the passage path D and snapped in a radial snap-in nose 106 in the throughflow channel. The permanent magnet 104 thus forms a cross section narrowing of the throughflow channel 96.

The permanent magnet 104 enables the use of ferromagnetic valve bodies 74, preferably in the form of a valve ball. Without further influence from the outside, the valve body 74 or the valve ball 74 therefore rests, due to the magnetic field originating from the permanent magnet 104, on the valve seat formation 76 of the seat component 78. The throughflow channel 96 is then barred to fluid passage by the valve body 74.

FIG. 6 shows a perspective view of a valve line arrangement with laboratory vessel 22 coupled thereto. The valve line arrangement comprises the previously described fluid line arrangement 12 and a switching arrangement 14. The switching arrangement 14 comprises a plurality of switching units 110, which have substantially the same structure, so that below only a single switching unit 110 is represented, as representative of the other switching units. The switching unit 110 comprises a permanent magnet 112 which can be shifted along a switching movement path B. More precisely, the permanent magnet 112 can be moved closer along the switching movement path to a fluid line element 16 and removed again from said fluid line element. The switching movement path B of the switching units 110 is preferably orthogonal to the channel path K, and the imaginary extension thereof intersects said channel path.

The permanent magnet 112 of a switching unit is preferably guided in a guide housing 114 for the movement along the switching movement path B. In addition, the guide housing 114 protects the permanent magnet 112 against environmental influences.

In the embodiment example represented in FIGS. 6 to 8, the guide housing 114, which, at one end, ends on the supporting structure accommodating the fluid line element 16, ends, at the other end, with a pneumatic drive device 116. The drive device 116 comprises a fixed cylinder 118 connected preferably to the guide housing 114 and a piston rod 120 which is movable in the cylinder along the switching movement path B relative to the cylinder 118. The piston rod 120 is preferably designed with dual action, so that, due a targeted pressure introduction on one of two sides of the piston 122, a targeted movement of the permanent magnet 112 closer to the fluid line element 16 associated with it and a removal therefrom can be performed.

Due to the movement of the permanent magnet 112 closer to the fluid line element 16 associated therewith, and due to the removal therefrom, it is possible, in a switching region 124 around the interface between switching movement path and channel path, to vary the magnetic field strength of the magnetic field originating from the permanent magnet 112.

As can be seen in FIG. 8, the imaginary extension of the switching movement path B toward the associated fluid line element 16 passes through the flow channel 62 of the associated fluid line element 62, preferably between the longitudinal end 70a of the throughflow body 70 located in the interior of the element body 60, and the site of the largest extension orthogonal to the channel path K of the valve body 74 abutting against the valve formation 72 located in the interior of the element body 60. This ensures that a lowering of the permanent magnet 122 associated with this valve seat formation 72, and the associated increase of the magnetic field strength in the associated switching region 124 causes a shift of the valve body 74 from the valve seat formation 76 to the abutment against the valve seat formation 72. Here it is also possible alternatively that the similar imaginary extension of the switching movement path B passes through the throughflow body 70, for example, close to the valve seat formation 72. Here, the builder has a certain amount of play in the arrangement of the switching unit 110. This play also depends on the shape and the thickness of the permanent magnets 112 used. However, for the average person skilled in the art, it will not present any problems at all to use reasonable testing efforts in order to determine the correct contact site in an individual case, for given permanent magnets in the approach position.

The fluid line element 16c providing a connection possibility for a laboratory vessel comprises, in the embodiment example depicted, as the only fluid element, a throughflow body, in each case both on the first throughflow opening 64 and also on the second throughflow opening 66. Thus, this fluid line element 16c comprises two valve seat formations located in the interior of the element body 60 thereof and facing the flow space of the fluid line element 16c. With each of these valve seat formations, a switching unit 110 is associated in each case, which, for space reasons, are provided on different, preferably opposite, sides of the fluid line arrangement 12. However, in the case of a corresponding thinner design of the permanent magnets 112, these two switching units 110 can also be located on a common side of the fluid line arrangement 12.

In the example depicted, the end-side fluid line elements 16*a* and 16*b* comprise only one flow space bent by 90°, but no supplementary flow channel.

In FIG. 7, the switching arrangement 14 is shown with all the switching units 110 in the inactive position, i.e., none of the permanent magnets 112 present has been moved closer to the fluid line arrangement 12. Consequently, all the valve bodies 74 are located on the valve seat formations 76 of the fluid line connection elements 24 connected to the respective fluid line elements 16. In the inactive state of the switching arrangement 14 shown in FIG. 7, this abutment against the valve seat formations 76 is achieved by means of the respective permanent magnets 104 in the throughflow channels 96 of the fluid line connection elements 24.

However, as shown in FIG. 8, when individual permanent magnets 112 are lowered toward the fluid line elements 16 associated with them or toward the valve seat formations 72 associated with them, then, in the also associated respective switching region 124, the magnetic field acting due to the permanent magnet 112 is so strong that the ferromagnetic valve body 74 is shifted by the permanent magnet 104 of the fluid line connection element 24 and thus away from the valve seat formation 76 toward the associated valve seat formation 72.

In the operating position of the switching arrangement 14 shown in FIG. 7, all the connection lines are each closed via the connecting pieces 18 and the line leading into the laboratory 22 by a valve body.

On the other hand, in the operating position of FIG. 8, the line leading into the vessel is open. In addition, the connection line of the second fluid line element 16, looking at FIG. 8, is open toward the right fluid element 16*c* coupled to the laboratory vessel 22. By means of an appropriate pressure buildup in the associated connection line, which can be released for a throughflow, it is thus possible to either introduce a fluid into the laboratory vessel 22 or remove it therefrom.

For a better orientation, it is pointed out that the connecting pieces known from FIGS. 1 and 2 are located in front of the drawing plane of FIGS. 7 and 8. The fluid line connection elements 24 connected to the respective fluid line elements 16 in FIGS. 7 and 8 are located in front of the drawing plane of FIGS. 7 and 8 and thus in front of the sectional plane of the section representations shown there. Therefore, the fluid line connection elements 24 cannot be seen in FIGS. 7 and 8.

Due to an appropriate switching of the valve-associated fluid line sections formed by the fluid line connection elements 24, fluid line elements 16 and valve body 74, it is not only possible to introduce different fluids into the connected laboratory vessels 22 and remove them therefrom, but it is also to clean the combined flow channel of the fluid line arrangement 12, for example, by running a clean fluid through the fluid line section.

Thus, with the present invention it is possible to supply several laboratory vessels from a single reservoir source with a respective fluid or to discharge used fluids from a plurality of laboratory vessels, without any resulting risk of cross-contamination of the laboratory vessel contents. Indeed, tests have shown that the cleaning rinsing by means of the modular constructed fluid line arrangement 12 according to the invention meets the highest cleanliness requirements.

In FIGS. 9 and 10, a second embodiment of a handling device according to the invention is shown. The reference numerals used for the description of the second embodiment are provided with an apostrophe to distinguish them from the reference numerals of the first embodiment.

In FIGS. 9 and 10, a valve line arrangement accommodated on a supporting structure 11' is marked in general with 10'. To this valve line arrangement 10', in FIGS. 9 and 10, a laboratory vessel 12' in the form of a cell culture vessel, for example, is coupled.

The valve line arrangement 10' comprises a line component 14', on which a fluid channel support 16' is provided in a manner so it can be rotated around a rotation axis R'.

On the fluid channel support 16', a plurality of fluid channel connection formations 18'—in the present example exactly six—(see FIG. 10) are accommodated, which are each run through by a fluid channel section 20'.

The fluid channel support connection formation 18', just like the other fluid channel support connection formations 19', is formed on a fluid channel support connecting piece 22' which, on the longitudinal end 24' thereof, is formed by the fluid channel connection formation 18', for the connection of a fluid line means 26', for example, in the form of a flexible tube.

In FIG. 9, for the differentiation of the fluid channel support connecting pieces 22' from one another, an additional connecting piece is marked with 28'. The fluid channel support connecting pieces are preferably constructed substantially identically.

As can be seen in FIG. 10, the line component 14' comprises a plurality of coupling formations 30*a'* to 30*d'*, four in the present example. The coupling formation 30*a'* is here designed for the temporary coupling of a fluid channel 32', which is provided in a manner which in itself is known in a cap 34' of the cell culture container 12'. The cap 34' comprises, for the coupling to the coupling formation 30*a'*, a cell culture container connection formation 36', which is substantially formed advantageously in agreement with the remaining connection formations, for example, the fluid channel support connection formation 18'.

The coupling formations 30*a'* to 30*d'* each preferably comprise a peripheral collar, in which the associated connection formation is embedded for the coupling to the respective coupling formation 30*a'* to 30*d'*. For the sake of clarity, only the collar 38' of the coupling formation 30*a'* is provided with a reference numeral.

In the present example, the coupling formations 30*b'* and 30*c'* are firmly and permanently coupled to connection formations 40*b'* and 40*c'* for the formation of a common fluid line section. For this purpose, the line component 14' can comprise a bracing body 46' or 48' run through by the fluid channel connecting piece 42' and 44', against which bracing body a clamping spring 50' or 52' is braced, which prestresses the connection formations 40*b'* or 40*c'* toward the respective coupling formations 306*b'* or 30*c'*. For this purpose, the bracing bodies 46' and 48' are connected preferably firmly to the line component 14'.

The connection formations 40*b'* and 40*c'* are run through by a fluid channel section 54' or 56', which are defined by the connecting pieces 42' and 44' which are formed on the respective longitudinal ends thereof which are located far from the connection formation 40*b'* or 40*c'*, again for the attachment of, in each case, a fluid line means, in this case a tube 58' or 60'.

In contrast to the connection formations 40*b'* and 40*c'*, which are firmly coupled to the coupling formations 30*b'* and 30*c'*, the coupling formation 30*d'* can be coupled to different connection formations of the fluid channel support 16' for the establishment of a common fluid line section. The coupling formation 30d' is referred to below as exchange coupling formation 30d'.

Since, in FIGS. 9 and 10, the fluid channel support connection formation 18'—which can only be seen in FIG. 10—of the fluid channel support 16' of the exchange coupling formation 30d' has been brought closest to the exchange coupling formation 30d', and this fluid channel support connection formation is therefore selected coupling connection formation 18' for the coupling to the exchange coupling formation 30d', the fluid channel support connection formation 18' is referred to as coupling connection formation 18' below. The latter is in a coupling position in FIG. 10, in which it is coupled to the exchange coupling formation 30d' for the formation of a common fluid line section which then passes through the coupling connection formation 18' and the exchange coupling formation 30d'.

The coupling connection formation 18' of FIG. 10 can be adjusted along a coupling path K' which is preferably parallel to the rotation axis R', in particular coupling axis K', between the coupling position shown in FIG. 10 and a coupling-ready position in which the coupling connection formation 18' is arranged along the coupling path K' at a distance from the exchange coupling formation 30d'. The coupling connection formation 18' is then accommodated deeper in the coaxial accommodation space 62' in the fluid channel support 16', so that the fluid channel support 16' can be rotated around the rotation axis R', without any associated risk of collision between the coupling connection formation 18' or another fluid channel support connection formation with the exchange coupling formation 30d'. In the coupling-ready position, the coupling connection formation 18' is preferably still in alignment with the exchange coupling formation 30d', so that the coupling connection formation 18' can be transferred by the shifting of same along the coupling path K' to the exchange coupling formation 30d' in a simple way by translation into the coupling position.

Just like the other fluid channel support connection formations, the coupling connection formation 18' can be prestressed by a prestressing device, for example, a coil spring 64', along the coupling path K' into the coupling position. In this case, the fluid channel support 16' comprises a force apparatus, not shown in FIGS. 9 and 10, which pulls back all the fluid channel support connection formations against the action of the respective compression springs associated with them into the respective accommodation spaces that are also associated with them. Preferably, the fluid channel support connection formations or the connecting pieces supporting them can be latched in the position retracted into the fluid channel support 16', for example, by a bayonet formation.

Alternatively, the fluid channel support connection formations can also be prestressed into the respective position retracted into the accommodation space 62', for example, when the coil spring 64' is a traction spring. In this case, at least the coupling connection formation 18' selected in each case for the coupling to the exchange coupling formation 30d' can be adjusted by a force apparatus, not shown in FIGS. 9 and 10, against the action of the prestressing spring 64' from the coupling-ready position into the coupling position shown in FIG. 10 and optionally latched in the coupling position against a return movement into the coupling-ready position.

One of the fluid channel support connection formations (see connecting pieces 22' and 28' in FIG. 9) can be selected by rotation of the fluid channel support 16' relative to the line component 14' as coupling connection formation, in that the respective fluid channel support connection formation is moved along a circular path A' as a selection path around the rotation axis R', until the selected coupling connection formation is in alignment with the exchange coupling formation 30d' and thus located in a coupling-ready position.

To facilitate the movement of the fluid channel support connection formations around the rotation axis R', a movement drive 66', particularly preferably an electric motor movement drive 66', is preferably provided on the line component 14', which is connected to the fluid channel support 16' in a manner so as to transmit movement and force, for example, via a gear drive 68'. For this purpose, a part of the outer peripheral surface 16a' (outside surface) of the fluid channel support 16' can be designed as a gear wheel or gear ring, preferably in the form of a single piece by plastic injection molding.

In the line component 14', a flow channel arrangement 70' is provided, which connects the fluid line sections 70a' to 70d' passing through the respective coupling formations 30a' to 30d' (to improve the clarity of the figure, only the fluid line sections 70a' and 70d' are provided with reference numerals) to one another in a fluid conducting manner. The fluid line sections 70b' and 70c', which are not marked individually, pass through the coupling formations 30b' or 30c' marked with the same lower case letters.

The flow channel arrangement 70' connects the fluid line sections 70a', 70b', 70c' and 70d' in the example represented in FIG. 10 parallel to one another in a so-called star pattern. In this design, in each case two of the fluid line sections 70a' to 70d' can be connected to one another in a fluid conducting manner, without the fluid line having to flow past the remaining fluid line sections along or on the coupling formations.

The connection formations 40b' and 40c', which are permanently coupled to the coupling formations 30b' and 30c', in FIG. 10, support preferably spherical valve bodies 72' (only the valve body 72' on the connection formation 40d' is provided with a reference numeral) which preferably comprise ferromagnetic material or are formed from ferromagnetic material. The line component 14' can comprise, in a manner which in itself is known, displaceable switching magnets which can be guided in cylinder guides 74a' to 74d' for the movement toward or the removal from the valve body 72', in order to displace the valve body 72' within the flow channel arrangement 70' by varying the magnetic field acting locally on them. The two valve bodies shown in FIG. 10 in the case of four coupling formations 30a' to 30d' are sufficient in order to always keep two coupling formations and thus the fluid line sections passing through them in fluid-conducting communication, while the remaining two coupling formations are barred to fluid conduction. In the absence of a magnetic field of switching magnets, the valve bodies 72' are prestressed by magnets 73a' to 73d' in the valve seats in the respective closed position.

For example, the fluid line 58' can be coupled to a disposal container, and the fluid line 60' can be coupled to a reservoir container for cleaning fluid.

The fluid channel connecting pieces 22', 28' as well as the fluid channel connecting pieces of FIG. 9, which are not further provided with reference numerals, can be coupled to different reservoir containers for media, for example, to a reservoir container for nutrient medium, to a reservoir container for a medium for detaching adhering cells from inner surfaces of the cell culture vessel and the like.

As shown in FIG. 9, the handling device for coupling the laboratory vessel 12' to the valve line arrangement 10' can comprise a moving part 13' represented with dashed lines.

This moving part can be in the form of a carriage or cart, for example. The moving part 13' is designed for the temporary accommodation of the laboratory vessel 12' and it can be moved closer along a connection path B' to the valve line arrangement 10' or removed from said valve line arrangement.

In order to be able to wet the inner surfaces of the laboratory vessel 12' with a fluid introduced into the laboratory vessel 12' in a targeted manner, it can be provided that the moving part 13' and the valve line arrangement 10' are arranged in a pivotal manner around a common pivot axis on a support frame—not represented—of the handling device, at least when the moving part 13' is arranged in a position moved close to the valve line arrangement 10'. As in the first embodiment, just as in the second embodiment, an electric motor drive can be provided as pivot drive. The related additional explanations concerning this first embodiment also apply to the second embodiment.

The invention claimed is:

1. A handling device for handling a laboratory vessel, the handling device comprising:
   a valve line assembly for introducing a fluid into the laboratory vessel and/or for discharging a fluid from the laboratory vessel; and
   a supporting structure receiving the valve line assembly, the valve line assembly including a line component, the line component including
      a first coupling that is run through by a first fluid line section, the first coupling being configured for a temporary coupling of a first fluid channel of the laboratory vessel to the first fluid line section,
      a second coupling that is run through by a second fluid line section, the second coupling being configured for a temporary or a permanent coupling of a second fluid channel of a fluid reservoir to the second fluid line section, and
      a third coupling that is run through by a third fluid line section, the third coupling being configured for a temporary or a permanent coupling of a third fluid channel of a discharge channel to the third fluid line section,
   wherein in the line component, a fluid channel assembly is formed, which connects each fluid line section of the first, of the second and of the third coupling to at least one fluid line section of one of the other two coupling for fluid transport between the first fluid line section and one of the second and the third fluid line sections, and
   wherein the second and third couplings comprise a valve seat and a valve body, and wherein the valve body rests on the valve seat in an operating state so as to prevent fluid passage through at least one fluid line section of the second coupling and the third coupling.

2. The handling device according to claim 1, wherein the valve line assembly comprises a fluid channel support which is movable relative to the line component and which comprises at least two fluid channel support connections, which are formed separately from one another and connected to different fluid channels for fluid transport, and which are each run through by a fluid channel section, and wherein at least one of the first, second and third couplings is a temporary common fluid line path with one of the at least two fluid channel support connections that is selected by relative movement of the line component and the fluid channel support.

3. The handling device according to claim 1, wherein in the flow channel assembly, to a side of the first coupling, the second coupling, the third coupling, the valve seat and the valve body are provided for a fluid mechanical separation of different regions of the flow channel assembly, wherein, in an operating state with regions of the flow channel assembly that are fluidically separated from one another, the valve body rests on the valve seat.

4. The handling device according to claim 1, wherein the valve body is formed at least partially from ferromagnetic material, and in that the valve seat comprises an annular magnet that surrounds the associated fluid line section and through which the fluid can flow, wherein the valve seat magnetically biases the valve body into a closed position in which the valve body rests on the valve seat.

5. The handling device according to claim 1, wherein the valve body comprises ferromagnetic material and the valve line assembly comprises a switching assembly with a variable magnetic field strength on the first coupling, the second coupling, and the third coupling so that the valve body is detachable from the valve seat.

6. The handling device according to claim 1, further comprising a moving part configured for temporary accommodation of the laboratory vessel and is movable with respect to the valve line assembly so as to define a connection path.

7. The handling device according to claim 6, wherein the moving part comprises an end wall oriented orthogonally to an approach path, and wherein the end wall defines a recess for receiving a neck section of a vessel neck of the laboratory vessel.

8. The handling device according to claim 6, wherein when the moving part is moved toward the valve line assembly, the moving part and the valve line assembly are pivotable on a support frame of the handling device around a common pivot axis which extends orthogonally to the connection path.

9. The handling device according to claim 8, wherein an electric motor cooperates with a pivot drive to transmit a drive force to a pivot shaft coupled to the support frame for common pivoting movement.

10. The handling device according to claim 9, wherein the pivot drive comprises a belt that runs around a pulley connected in a rotationally fixed manner to the pivot shaft, and/or a gear drive.

11. The handling device according to claim 9, wherein the pivot drive is coupled directly to the pivot shaft.

* * * * *